United States Patent
Zacher

(10) Patent No.: US 11,712,333 B2
(45) Date of Patent: Aug. 1, 2023

(54) IOL BASE COMPRESSION DEVICE HAVING AN IOL TOWING MECHANISM

(71) Applicant: Alcon Inc., Fribourg (CH)

(72) Inventor: Rudolph F. Zacher, Trabuco Canyon, CA (US)

(73) Assignee: Alcon Inc., Fribourg (CH)

( * ) Notice: Subject to any disclaimer, the term of this patent is extended or adjusted under 35 U.S.C. 154(b) by 351 days.

(21) Appl. No.: 16/896,123

(22) Filed: Jun. 8, 2020

(65) Prior Publication Data

US 2020/0405476 A1 Dec. 31, 2020

Related U.S. Application Data

(60) Provisional application No. 62/867,349, filed on Jun. 27, 2019.

(51) Int. Cl.
*A61F 2/16* (2006.01)

(52) U.S. Cl.
CPC ............ *A61F 2/1678* (2013.01); *A61F 2/167* (2013.01); *A61F 2002/1681* (2013.01)

(58) Field of Classification Search
CPC . A61F 2/1678; A61F 2/167; A61F 2002/1681
See application file for complete search history.

(56) References Cited

U.S. PATENT DOCUMENTS

| | | | |
|---|---|---|---|
| 10,010,408 B2 | 7/2018 | Auld | |
| 2006/0241650 A1 | 10/2006 | Weber et al. | |
| 2009/0171366 A1* | 7/2009 | Tanaka | A61F 2/1664 606/107 |
| 2015/0342726 A1* | 12/2015 | Deacon | A61F 2/1664 623/4.1 |
| 2017/0172727 A1* | 6/2017 | Kanner | A61F 2/1672 |
| 2018/0368971 A1* | 12/2018 | Zacher | A61F 2/167 |
| 2019/0151078 A1 | 5/2019 | Watanabe et al. | |
| 2020/0197168 A1* | 6/2020 | Wu | A61F 2/1678 |

FOREIGN PATENT DOCUMENTS

EP 2062552 A1 5/2009

\* cited by examiner

*Primary Examiner* — Jerrah Edwards
*Assistant Examiner* — Aren Patel
(74) *Attorney, Agent, or Firm* — Patterson + Sheridan, LLP

(57) ABSTRACT

An IOL base compression device having an IOL towing mechanism is described.

23 Claims, 17 Drawing Sheets

IOL BASE COMPRESSION DEVICE HAVING AN IOL TOWING MECHANISM

CROSS-REFERENCE TO RELATED APPLICATIONS

This application claims priority to and benefit of U.S. Provisional Patent Application No. 62/867,349, filed Jun. 27, 2019, the entire contents of which are incorporated by reference in their entirety.

TECHNICAL FIELD

The present disclosure relates to systems, apparatuses, and methods for intraocular lens (IOL) injectors.

BACKGROUND

The human eye in its simplest terms functions to provide vision by transmitting and refracting light through a clear outer portion called the cornea, and further focusing the image by way of the lens onto the retina at the back of the eye. The quality of the focused image depends on many factors including the size, shape, and length of the eye, and the shape and transparency of the cornea and lens. When trauma, age, or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens (IOL).

Many cataractous lenses are removed by a surgical technique called phacoemulsification. During this procedure, an opening is made in the anterior capsule of an eye and a phacoemulsification cutting tip is inserted into the diseased lens and vibrated ultrasonically. The vibrating cutting tip liquifies or emulsifies the lens so that the lens may be aspirated out of the eye. The diseased lens, once removed, is replaced with an IOL.

The IOL may be injected into the eye through a small incision, sometimes the same incision used to remove the diseased lens. An IOL injector may be used to deliver an IOL into the eye.

SUMMARY

According to a first aspect, an IOL compression device is described. The IOL compression device has a housing having a proximal end and a distal end, and a track disposed on a first side of the housing. The IOL compression device also has a tapered IOL compression channel disposed within the housing and having a longitudinal axis extending from the proximal end to the distal end. The IOL compression device also has a slidable button movably coupled within the track, the button axially slidable between a proximal position and a first distal position, the track having a longitudinal axis substantially aligned with and adjacent to the tapered IOL compression channel. The slidable button has a pad accessible to a user and adapted to receive an axial force, and an IOL base towing post having a first end coupled to the button and a second end adapted to contact a distal inner edge of an IOL base when the IOL base is in the compression channel. In response to an axial movement of the button toward the distal end of the housing, the IOL base towing post is adapted to axially pull the IOL base through the tapered IOL compression channel toward the distal end of the housing, and in response to contacting an interior surface of the tapered IOL compression channel, the IOL base is adapted to adopt a compressed configuration.

The IOL towing post may include a hinge, the IOL compression channel may include a hard stop disposed within the tapered IOL compression channel at the distal end of the housing and contactable by the IOL base towing post when the button is in the first distal position, the track may include a second distal position distal to the first distal position, and the button may be axially slidable to the second distal position. In response to an axial movement of the slidable button to the second distal position, the IOL base towing post may be adapted to fold at the hinge in response to contacting the hard stop and the IOL base towing post may be thereby configured to exit the tapered IOL compression channel after the IOL base adopts the compressed configuration.

The track may include a second distal position distal to the first distal position, the button may be axially slidable to the second distal position, and a portion of the track between the first distal position and the second distal position may include a ramp having a slope that inclines away from the IOL compression channel. In response to an axial movement of the slidable button along the ramp to the second distal position, the IOL base towing post may be adapted to exit the tapered IOL compression channel after the IOL base adopts the compressed configuration.

The housing may include a recess sized to receive the IOL base towing post, the recess located at the first distal position. The button may include a spring adapted to move the IOL towing post into the recess, the spring having a first end coupled to the button and a second end coupled to the IOL towing post. In response to an axial movement of the slidable button to the first distal position, the IOL towing post may be transversely movable into the recess in response to movement of the spring and thereby exits the IOL compression channel after the IOL base adopts a compressed configuration.

The inner edge of the IOL base may include a groove disposed within the circumference of the inner edge and the second end of the IOL base towing post may have a size and shape adapted to insert into the groove in the distal inner edge of the IOL.

The distal inner edge of the IOL base may include a notch and the second end of the IOL base towing post may have a size and shape adapted to insert into the notch.

The slidable button may include a second post having a first end coupled to a proximal portion of the slidable button, wherein the second post is coupled to the slidable button at a first distance from the IOL base towing post such that when the IOL base towing post contacts the distal inner edge of the IOL base, the second post is proximally adjacent to a trailing haptic of the of the IOL base.

The second post may include a hinge adapted to fold laterally in response to contacting a plunger tip moving axially through the compression channel, the second post thereby configured to exit the tapered compression channel.

The IOL compression device may be adapted to be fixedly disposed within or removably disposed within an IOL injector. The IOL injector may include an injector body including a main body having a proximal end and a distal end, and a nozzle having a proximal end and a distal end, the proximal end of the nozzle coupled to the distal end of the main body. The nozzle may have an IOL storage location configured to house an uncompressed IOL, and an IOL dwell location distal to the IOL storage location. The injector body may have a bore having a longitudinal axis extending from the proximal end of the main body to the distal end of the nozzle. The IOL injector may include a plunger movably coupled within the injector body and aligned within the bore, the plunger having a plunger tip adapted to contact an IOL.

The IOL compression device may be disposed within the nozzle.

The IOL base may be in an IOL storage location when the button is at the proximal position, and the IOL base may be in the dwell location when the button is at the first distal position.

The tapered IOL compression channel may be coupled to and aligned with the bore, and the plunger may be axially movable through the tapered IOL compression channel.

According to a second aspect, an IOL compression device is described. The IOL compression device has a housing having a proximal end and a distal end, and a beam track disposed on a first side of the housing. The IOL compression device also has a tapered IOL compression channel disposed within the housing and having a longitudinal axis extending from the proximal end to the distal end. The IOL compression device also has a slidable beam movably coupled within the beam track, the slidable beam axially slidable therein between a proximal position and a first distal position, the beam track having a longitudinal axis substantially aligned with and adjacent to the tapered IOL compression channel. The IOL compression device has an IOL base towing post having a first end coupled to a distal portion of the slidable beam and a second end adapted to contact a distal inner edge of an IOL base when the IOL base is in the compression channel. The IOL compression device also has a second post having a first end coupled to a proximal portion of the slidable beam, wherein the second post is coupled to the slidable beam at a first distance from the IOL base towing post such that when the IOL base towing post contacts the distal inner edge of the IOL base, the second post is proximally adjacent to a trailing haptic of the IOL base. In response to an axial force applied to the second post toward the distal end of the housing, the slidable beam is adapted to slide axially within the beam track toward the distal end of the housing, the IOL towing post is adapted to pull the IOL base through the IOL compression channel toward the distal end of the housing, and in response to contacting an interior surface of the IOL compression channel, the IOL base is adapted to adopt a compressed configuration.

The beam track may include a second distal position distal to the first distal position, the slidable beam may be axially slidable to the second distal position, and a portion of the beam track between the first distal position and the second distal position may include a well sized to receive the slidable beam. In response to a axial movement of the slidable beam to the second distal position, the slidable beam may be adapted to enter the well, and the IOL base towing post and the second post may be configured to exit the tapered IOL compression channel after the IOL base adopts the compressed configuration.

The inner edge of the IOL base may include a groove disposed within the circumference of the inner edge and the second end of the IOL base towing post may have a size and shape adapted to insert into the groove in the distal inner edge of the IOL base.

The distal inner edge of the IOL base may include a notch and the second end of the IOL base towing post may have a size and shape adapted to insert into the notch.

The IOL compression device may be adapted to be fixedly disposed within or removably disposed within an IOL injector. The IOL injector may include an injector body having a main body having a proximal end and a distal end, and a nozzle having a proximal end and a distal end, the proximal end of the nozzle coupled to the distal end of the main body. The nozzle may have an IOL storage location configured to house an uncompressed IOL, and an IOL dwell location distal to the IOL storage location. The IOL injector may also have a bore having a longitudinal axis extending from the proximal end of the main body to the distal end of the nozzle, and a plunger movably coupled within the injector body and aligned within the bore, the plunger having a plunger tip adapted to contact an IOL.

The IOL compression device may be disposed within the nozzle.

The IOL base may be in an IOL storage location when the slidable beam is at the proximal position, and the IOL base may be in a dwell location when the slidable beam is at the first distal position.

The tapered IOL compression channel may be coupled to and aligned with the bore, and the plunger may be axially movable through the tapered IOL compression channel. In response to an axial movement of the plunger toward the distal end of the nozzle, the plunger tip may be adapted to contact the second post; the slidable beam may be adapted to slide axially within the beam track to a first distal position, the IOL towing post may be adapted to pull the IOL base toward the distal end of the nozzle, and in response to contacting an interior surface of the IOL compression channel, the IOL base may be adapted to adopt a compressed configuration.

A portion of the beam track between the first distal position and the second distal position may include a well sized to receive the slidable beam. In response to a further axial movement of the plunger toward the distal end of the nozzle, the slidable beam may be adapted to enter the well, the IOL base towing post and the second post may be adapted to exit the tapered IOL compression channel after the IOL base adopts the compressed configuration, and the plunger tip may be adapted to contact the IOL base, such that the plunger may be adapted to axially advance the IOL to exit the distal end of the nozzle.

BRIEF DESCRIPTION OF THE DRAWINGS

For a more complete understanding of the present disclosure, reference is now made to the following description, taken in conjunction with the accompanying drawings, which are not to scale, and in which.

DETAILED DESCRIPTION

Figure 1:
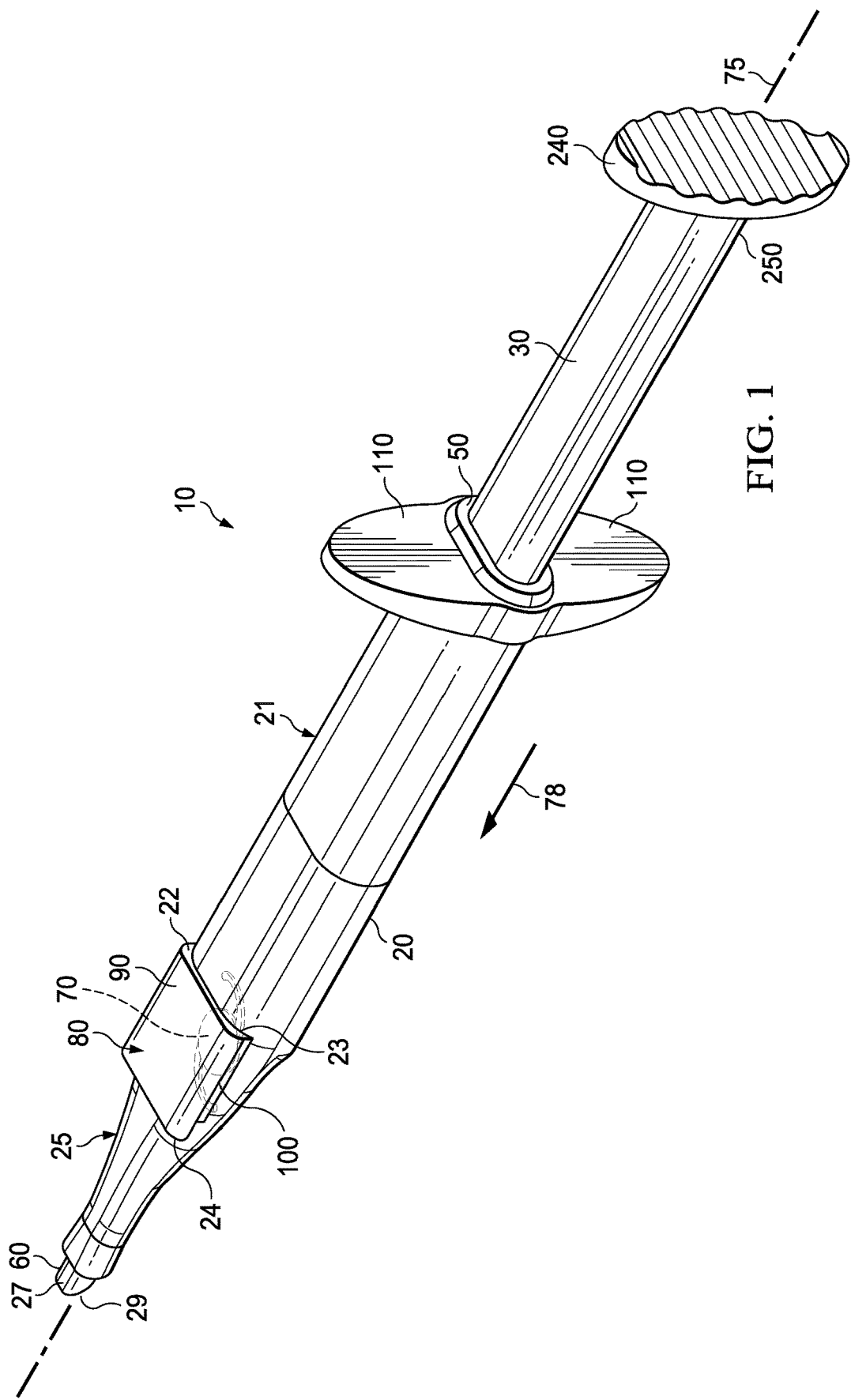
FIG. 1 is a perspective view of an example IOL injector.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

Figure 2:
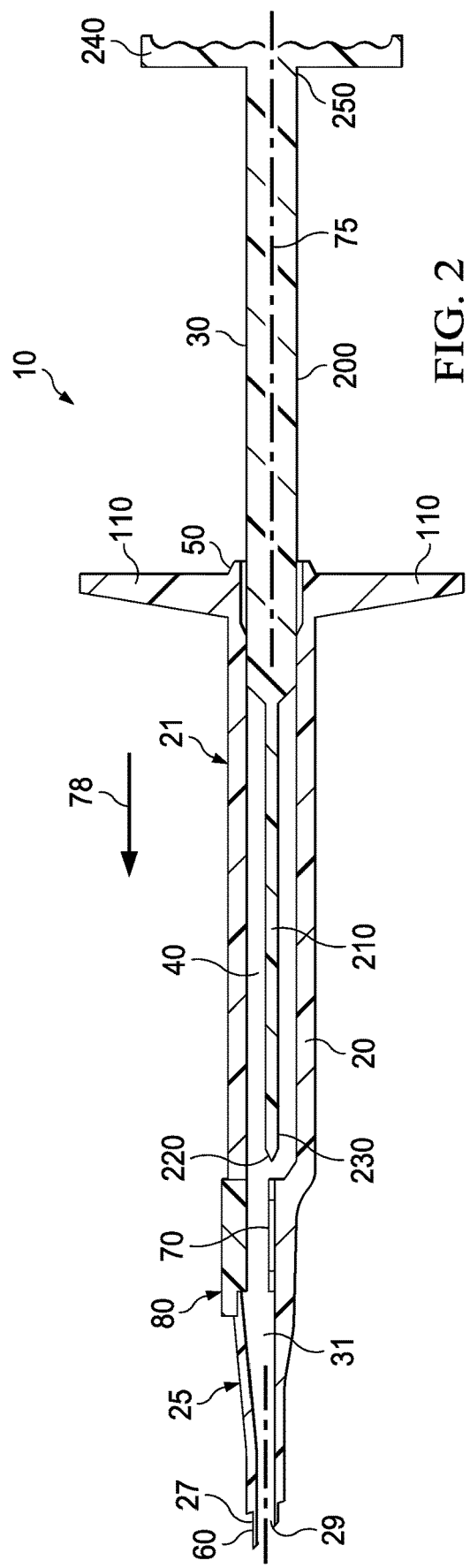
FIG. 2 is a longitudinal cross-sectional view of the example IOL injector of FIG. 1.

FIGS. 1 and 2 are schematics of an example IOL injector 10 that is actuated by manual user application of force. The IOL injector 10 includes an injector body 20, a plunger 30 adapted to reciprocate through a bore 40 formed in the injector body 20. The injector body 20 has a main body 21 having a proximal end 50 and a distal end 23, and a nozzle 25 having a proximal end 22 and a distal end 60. The proximal end 22 of the nozzle 25 is coupled to the distal end 23 of the main body 21. The nozzle 25 has an IOL storage location 80 configured to house an uncompressed IOL 70, and an IOL dwell location 809 distal to the IOL storage location 80.

The bore 40 extends from the proximal end 50 of the main body 21 to the distal end 60 of the nozzle 25. A distal portion of the bore 40 within the nozzle 25 forms a delivery channel 31 through which an IOL may be axially advanced, compressed, and delivered into an eye via an opening 29 in distal tip 27 at distal end 60.

The plunger 30 is movably coupled within the injector body 20 and aligned within the bore 40. The plunger 30 has a plunger tip 220 adapted to contact an IOL 70.

The IOL injector 10 also includes a longitudinal axis 75. The longitudinal axis 75 may extend along the plunger 30 and define a longitudinal axis of the plunger 30.

The IOL storage location 80 may include a door 90 to provide access to the interior of the IOL storage location 80. The door 90 may include a hinge 100 such that the door 90 may be pivoted about the hinge 100 to open the IOL storage location 80 and, for example, allow the installation of the IOL 70. In other implementations, the IOL storage location 80 may exclude a door for installing the IOL 70. In such instances, the IOL 70 may be incorporated into the IOL storage location 80 at the time of assembly of the IOL injector 10. Thus, in such instances, the IOL injector 10 would be a preloaded IOL injector. In such instances, the IOL storage location 80 may have a cover that is not configured to open, rather than a door 90. The IOL storage location 80 may include a hole 102 adapted to allow addition of viscoelastic into the IOL storage location 80.

The injector body 20 may also include tabs 110 formed at the proximal end 50 of the injector body 20. The tabs 110 may be manipulated by fingers, thumb, or hand of a user, such as an ophthalmologist, an ophthalmic surgical assistant or nurse, or other medical professional, to advance the plunger 30 through the bore 40.

The plunger 30 may include a plunger body 200, a plunger rod 210 extending distally from the plunger body 200, and a plunger tip 220 formed at the distal end 230 of the plunger rod 210 and adapted to contact an IOL disposed, for example, with the IOL storage location 80 of the IOL injector 10. As the plunger 30 is axially advanced and thereby displaced distally within the bore 40 in the direction of the arrow 78, the plunger tip 220 of the plunger 30 is adapted to engage and advance the IOL, such as IOL 70. In FIGS. 1 and 2, the IOL 70 is shown located within the IOL storage location 80. The plunger 30 may also include flanges 240 formed at proximal end 250, which may be manipulated by the fingers, thumb, or hand of a user to advance the plunger 30 through the bore 40 by displacing the plunger 30 through the bore 40 distally in the direction of the arrow 78.

Figure 3A:
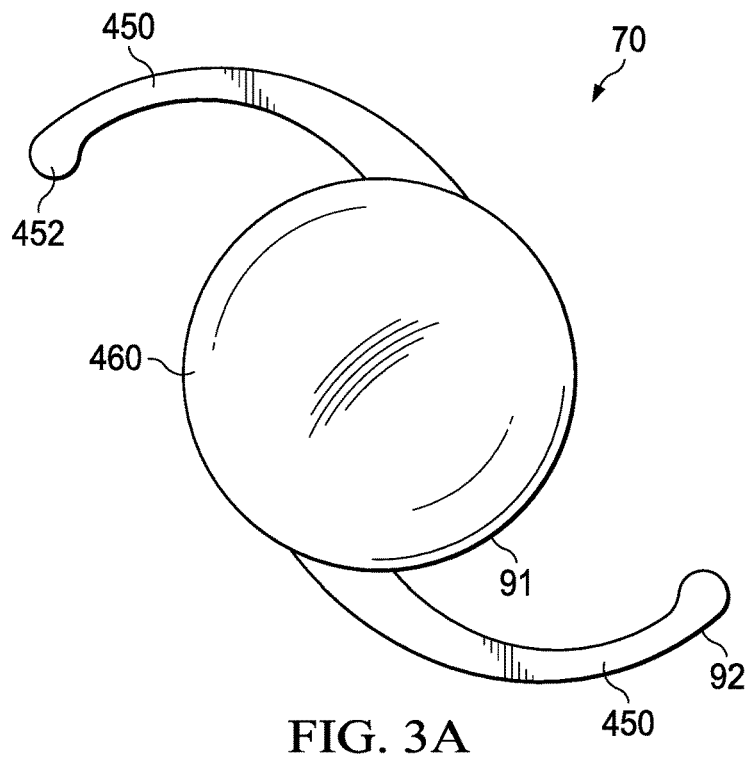
FIG. 3A shows an example one-piece IOL.

In some implementations, the IOL 70 may be a one-piece IOL. That is, in some implementations, the IOL 70 may include an optic 460 and haptics 450, as shown in FIG. 3A. Each of the haptics 450 include a tip 452. In some implementations, the optic 460 and the haptics 450 may be integrally formed out of a single piece of material. In other implementations, the optic 460 may be formed out of one piece of material; the haptics 450 may be formed out of another piece of material, and the optic 460; and the haptics 450 may be coupled together prior to delivery into an eye. In some instances, the optic 460 and haptics 450 may be fixedly secured to each other prior to insertion into an IOL injector and delivered into an eye.

Figure 3B:
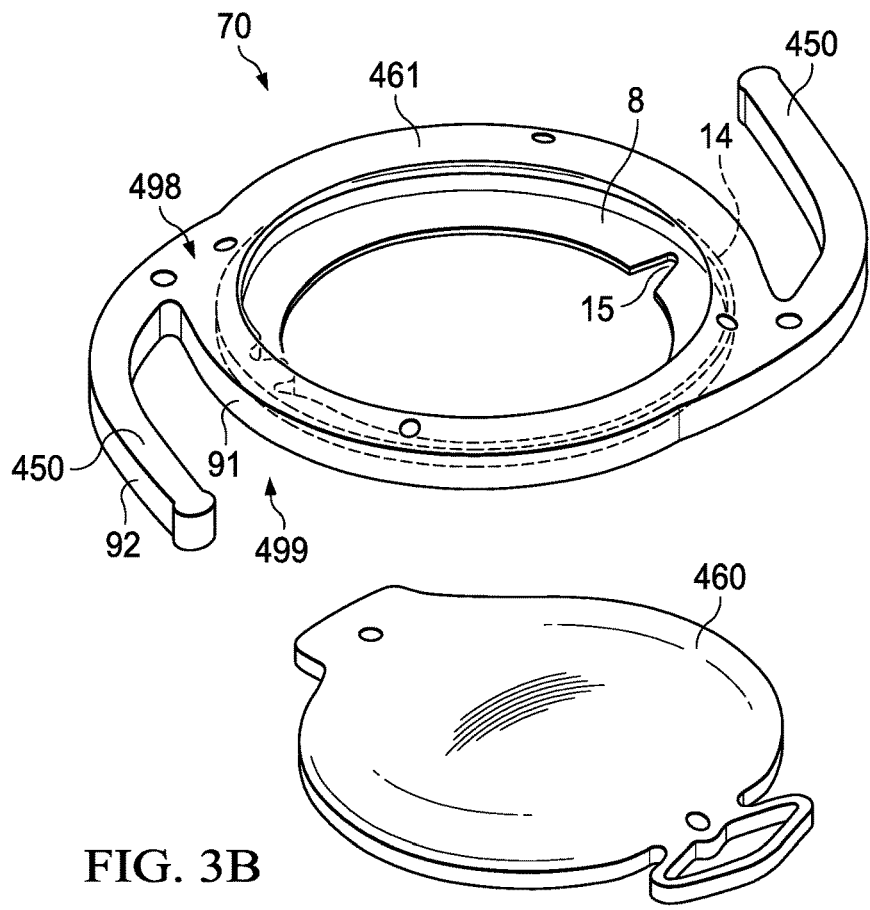
FIG. 3B shows an example two-piece IOL including a base and an optic.
Figure 4:
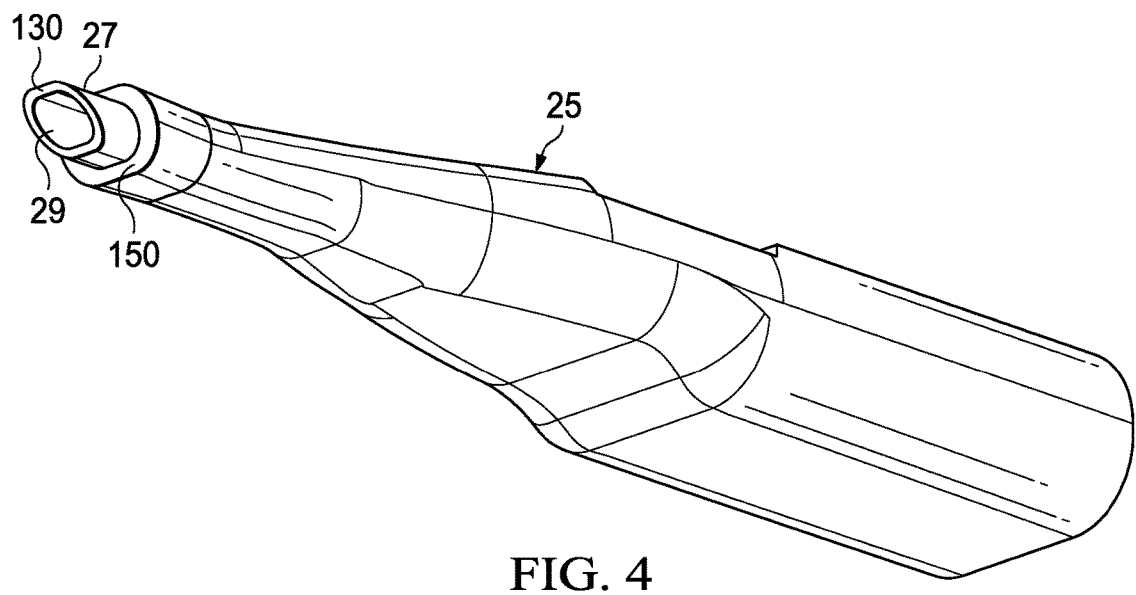
FIG. 4 is a perspective view of an example nozzle of an IOL injector.
Figure 5A:
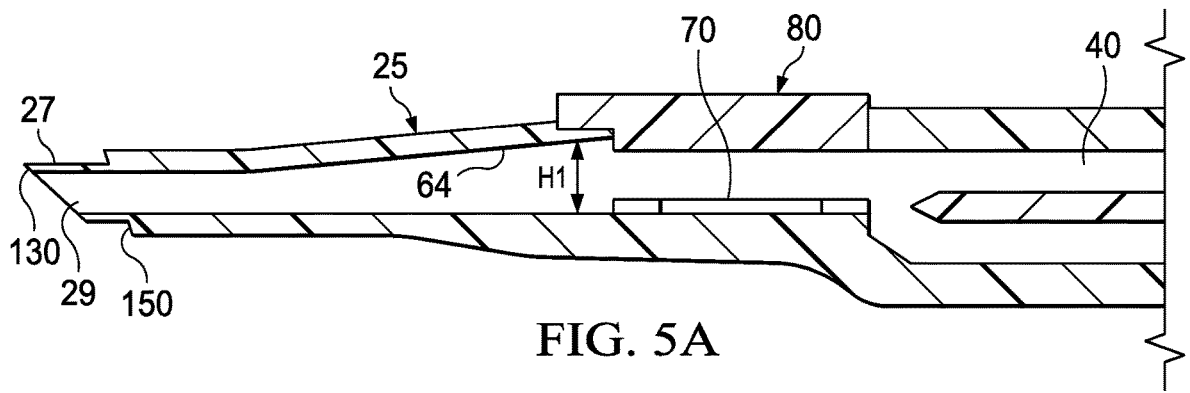
FIG. 5A is a cross-sectional view of the nozzle of the IOL injector of FIG. 4.
Figure 5B:
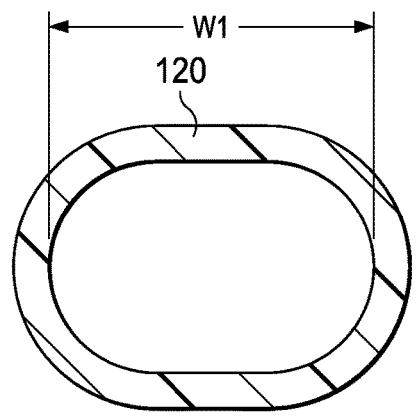
FIG. 5B is another cross-sectional view of the nozzle of the IOL injector of FIG. 4.

In other implementations, the IOL 70 may be a multi-piece IOL, as shown, for example, in FIG. 3B. For example, in some implementations, the IOL 70 be include two or more separate components. FIG. 3B is an example IOL 70 that includes two removably attached components. As shown in FIG. 3B, the IOL 70 includes an optic 460 and a base 461 that includes haptics 450 and that has a top 498 and a bottom 499. The optic 460 and the base 461 are adapted to be coupled together to form a unitary IOL. For example, in some instances, the optic 460 and the base 461 are adapted to be coupled together to form a unitary IOL such as prior to implant, or after implant inside an eye. In some instances, the optic 460 can be detached from the base 461 and be replaced, if desired. In some instances, one or more components of a multi-piece IOL, such as, for example the two-piece IOL 70 shown in FIG. 3B, are separately injectable into a patient's eye. Once in the eye, the components may be assembled into a complete IOL. For example, in the case of the two-piece IOL 70 shown in FIG. 3B, the optic 460 and the base 461 are separately injectable into an eye. Once injected, the optic 460 is adapted to be coupled to the base 461 within the groove 14 disposed within an inner edge 8 of the base 461. In some instances, one or more notches 15 are disposed within the outer edge 8. The one or more notches 15 may be configured for coupling with the optic 460 and thereby orienting assembly of the optic 460 onto the base 461. The notches 15 may also provide an initiation point for the IOL base 461 to begin folding or adopting a compressed conformation. In particular, in some instances, the notches 15 are disposed within the inner edge 8 such that the IOL base 461 adopts a compressed conformation wherein the distal and proximal haptics 450 are each respectively maintained in a distal and a proximal position within the IOL injector as the IOL base 461 adopts the compressed conformation. In some instances, for example, the base 461 can have two notches 15, disposed on opposite sides within the inner edge 8, for example one notch 15 disposed within the inner edge 8 at a position adjacent to a midpoint of the length of the distal haptic 450 and another notch 15 disposed within the inner edge 8 at a position adjacent to a proximal haptic 450. The notches 15 may have other functionality. For example, in some instances, a user may contact the notches 15 with a surgical instrument in order to manipulate the base 461 position during implantation.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into an IOL storage compartment of the IOL injector, such as the IOL storage location 80 of the IOL injector described above. As also explained, the IOL storage location 80 may be accessed via a door, such as the door 90.

In the case of a two-piece IOL, in some implementations, a user may load the base, such as base 461, into an IOL storage compartment of an IOL injector, for example, via a door. The optic such as optic 460, may be introduced into the IOL storage compartment of a separate IOL injector, for example, via a door. In some instances, the IOL storage compartment may be accessed through the door such as door 90.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration) is loaded into the IOL injector not by a user, but, rather, the IOL is installed in the IOL injector before and is already contained within the IOL injector when the IOL injector is received by the user. The IOL injector(s) may be packaged within sterile packaging when received by a user.

As would be understood by persons of ordinary skill in the art upon reading the present disclosure, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. For example, manual installation and folding of an IOL may also introduce the possibility of contamination of the IOL, such as by human error or poor sterile technique. Contamination of the IOL may compromise the sterile environment for the patient and risk infection or other harm to the patient.

FIGS. 4-7 illustrate details of the example nozzle 25. In some instances, the nozzle 25 has a tapered exterior surface. Further, the nozzle 25 may include a portion of the bore 40 forming a delivery channel 31 that tapers towards the opening 29. The distal tip 27 is adapted for insertion into an eye so that the IOL 70 may be implanted. The IOL 70 is expelled from the opening 29 formed in the distal tip 27 into the eye. As shown in FIG. 5B, delivery channel 31 and the distal tip 27 may have an elliptical cross section 120 having a width W1. Additionally, the distal tip 27 may include a beveled tip 130. The IOL storage location 80, delivery channel 31, and opening 29 may define a delivery passage. A size of the delivery passage may vary along its length. For example, in some instances, the width W1, a height H1, or both, of the delivery passage may change along a length of the delivery passage. The variation in size of the delivery passage may contribute to the compression of the IOL as it is advanced therealong through the delivery passage.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 6:
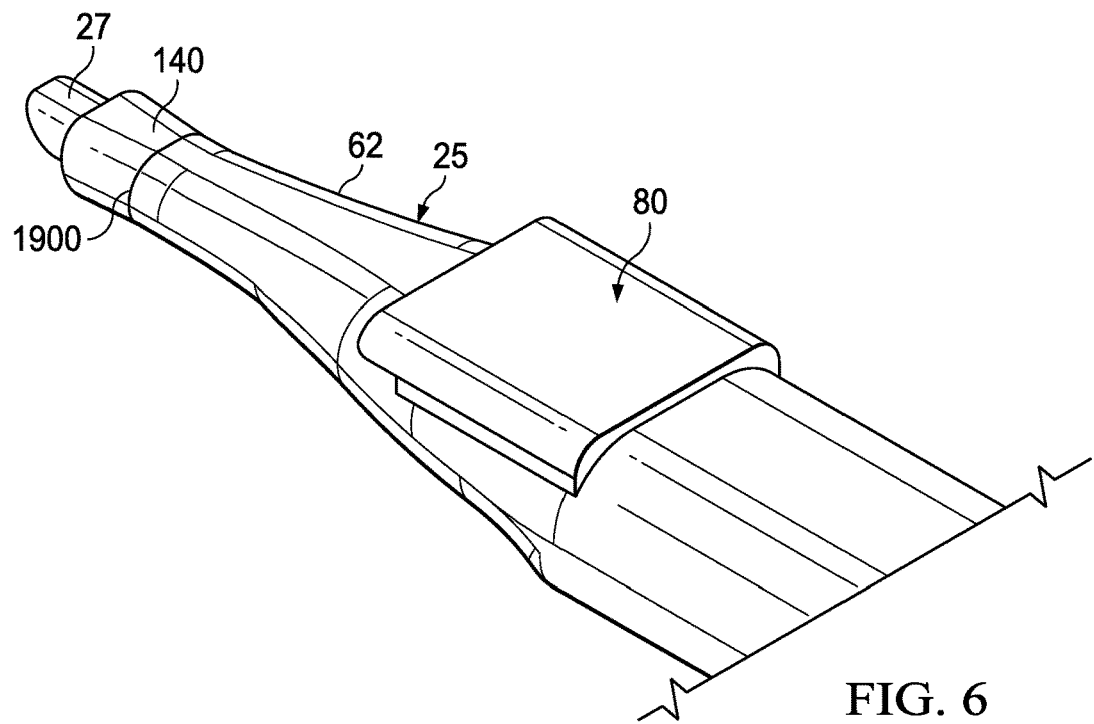
FIG. 6 is another perspective view of the nozzle of the IOL injector of FIG. 4.
Figure 7:
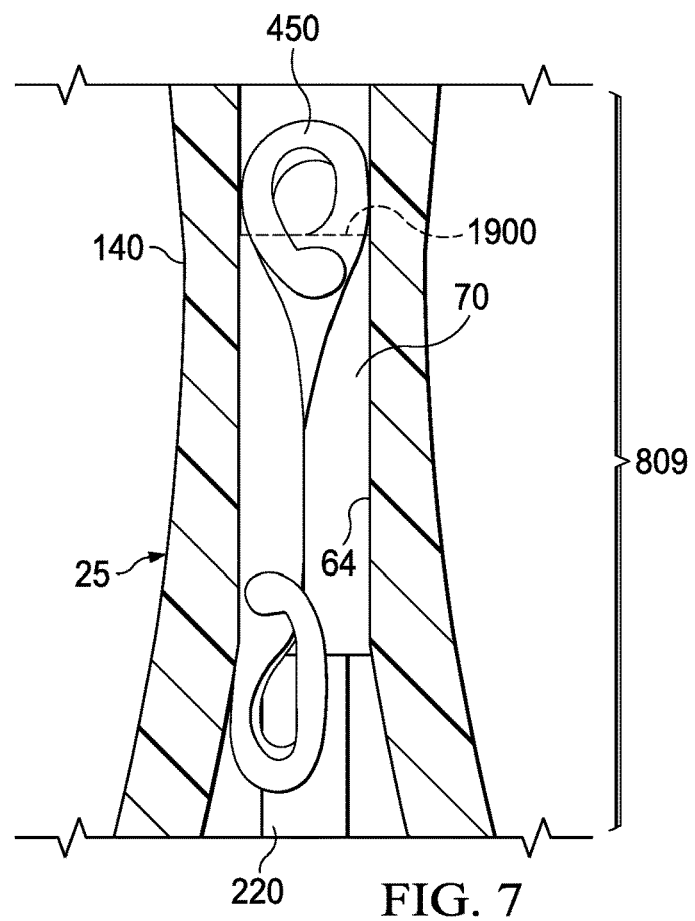
FIG. 7 is a view of a distal end of an example IOL injector with an IOL located therein and positioned in a dwell location.
Figure 8:
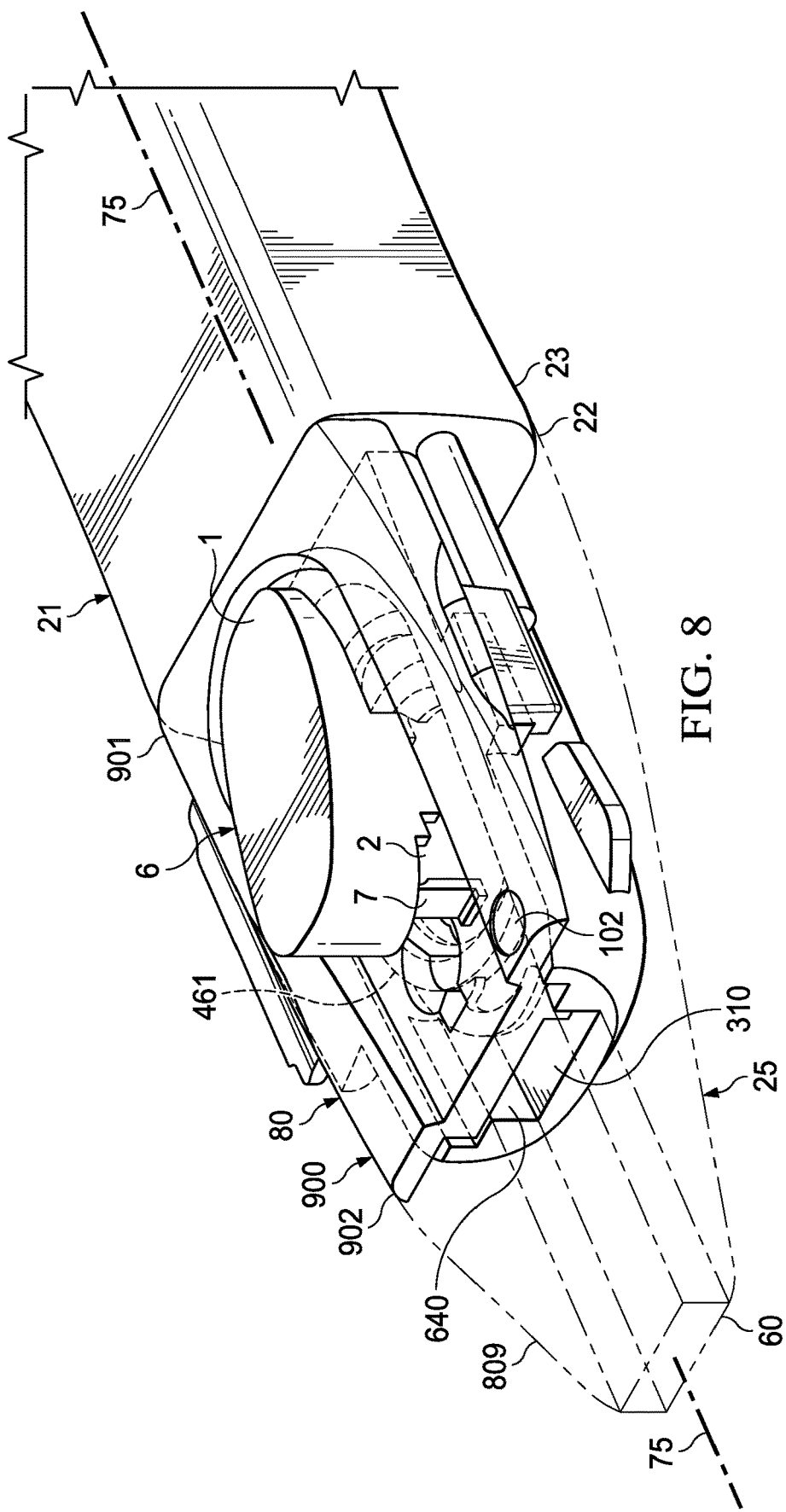
FIG. 8 is a perspective view of an example IOL compression device disposed within an example IOL injector with an IOL base located therein.

FIG. 6 and FIG. 7 are detail views of a portion of the example nozzle 25. The nozzle 25 may include a tapered portion 62 and the insertion depth guard 140. The distal tip 27 may include a demarcation 1900 that provides a visual indication of a dwell location 809 of a compressed or partially compressed IOL 70. The term "dwell location" as used herein refers to a location adjacent to the distal end 60 of the nozzle 25. For example, the dwell location 809 may be a location 2-10 mm from the distal end 60. For example, in the example shown in FIG. 6, the demarcation 1900 is a narrow ridge or line that encircles all or a portion of the nozzle 25. In some instances, the demarcation 1900 may be disposed between the tapered portion 62 and the insertion depth guard 140. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as it is moved therethrough by the plunger 30.

FIG. 7 shows a view of the distal end 60 of the IOL injector 10 with an IOL 70 located therein at a dwell position 809 in nozzle 25. As shown in FIG. 7, the dwell position 809 of the IOL 70 may be defined as a location where a distal edge of the optic of the IOL 70 substantially aligns with the demarcation 1900. A haptic 450 or a portion thereof may extend beyond the demarcation 1900.

In various implementations described herein, the IOL injector 10 includes an IOL compression device configured to couple to an uncompressed IOL base 461 and axially advance the base 461 through a tapered IOL compression channel 310 disposed within the IOL compression device, and in response, the uncompressed IOL base 461 is adapted to contact an interior surface 640 of the tapered IOL compression channel 310 and adopt a compressed configuration.

In various implementations, the IOL compression device described herein is contained within an IOL compression device housing 900 having a proximal end 901 and a distal end 902. The housing 900 may form an integral part of an IOL injector body 20, such as fixedly disposed within and forming an integral part of the nozzle 25, the IOL storage location 80, or the main body 21. In other instances, the IOL compression device may be a separate component contained within the housing 900, such as a detachable component that may be removably connected to an IOL injector. The housing 900 of the IOL compression device may be adapted to be removably disposed within the injector body 20 of an IOL injector 10, such as within the nozzle 25, within the IOL storage location 80, or within the main body 21.

In some implementations, when the IOL compression device is disposed within an IOL injector, such as within the nozzle of an IOL injector, the IOL compression channel 310 has a longitudinal axis 75 and may be coupled to and aligned with the bore 40, and the plunger 30 may be axially movable through the tapered IOL compression channel 310, thereby allowing axial advancement of a compressed IOL base 461 to the distal end 60 of the nozzle 25 and into an eye of a patient.

In various implementations, the IOL compression device described herein is configured to axially advance the IOL base 461 by "towing" the IOL base 461 axially through the tapered IOL compression channel 310. Accordingly, in certain implementations, the IOL compression device described herein utilizes a different principle of operation from that of traditional plungers, which typically compress an IOL by contacting the IOL at a proximal outer edge 91 and/or a proximal outer edge of a trailing haptic 92 and axially "push" an IOL through the bore 40 by applying an axial force to the proximal outer edge 91/92 of an IOL and/or trailing haptic thereof. The term "trailing haptic" as used herein refers to a haptic of an IOL or an IOL base that is closer to the proximal end of an IOL compression device or an IOL injector when the IOL or IOL base is disposed within an IOL compression device or IOL injector.

As would be understood by skilled persons upon reading the present disclosure, the terms "tow" or "towing" as used herein generally refer to contacting or coupling a first component to one or more additional components, such that the one or more additional components may be pulled by the first component, upon movement of the first component. In particular, as used herein, the present disclosure relates to certain embodiments of an IOL compression device that utilizes a component, such as a slidable button or a slidable beam adapted to contact or couple to and tow an IOL 70 such as an IOL base 461 at through an IOL compression channel 310.

By utilizing the towing mechanism described herein, the IOL compression device described herein can prevent "bunching" of an IOL within an IOL injector. The term "bunching" as used herein refers to unwanted axial folding or compression in the longitudinal axis of an IOL 70 that may sometimes occur when a traditional plunger is used to advance the IOL 70 through the delivery channel of an IOL injector. In particular, the bunching may sometimes occur when using a traditional plunger to advance an IOL 70 through the tapered delivery channel 31 of the nozzle 25, such as from a storage location 80 to a dwell location 809.

FIG. 8 to FIG. 10E are schematics of example IOL compression devices having a slidable button. In some implementations, the IOL compression device has a slidable button 1 movably coupled within a track 2 adapted to allow axial sliding movement of the slidable button 1 therein. The track 2 is disposed on a first side of the housing 900, such as an upper side of the housing 900. The button is axially slidable therein, such as between a proximal position 3 and a first distal position 4. The track 2 has a longitudinal axis 75 substantially aligned with and adjacent to the tapered IOL compression channel 310. The slidable button 1 has a pad 6 accessible to a user and adapted to receive an axial force, such as applied by a finger or a thumb of a user. The slidable button 1 has an IOL base towing post 7 having a first end coupled to the button 1 and a second end adapted to contact or couple to a distal inner edge 8 of an IOL base 461. In general, the IOL compression device of the present disclosure is suitable for use with IOLs having a structure that provides a distal point of contact or coupling with an IOL, similar to the distal inner edge 8 of the IOL base 461. FIG. 3B illustrates an example distal inner edge 8 of an IOL base 461. As would be understood, the distal inner edge 8 is the inner edge of the IOL base 461 when placed in the IOL compression device that is closer to the distal end 902 of the IOL compression device. For example, when the IOL compression device is disposed within an IOL injector, the distal inner edge 8 is the inner edge of the IOL base 461 that is closer to the distal end 60 of the injector body 20.

Figure 10A:
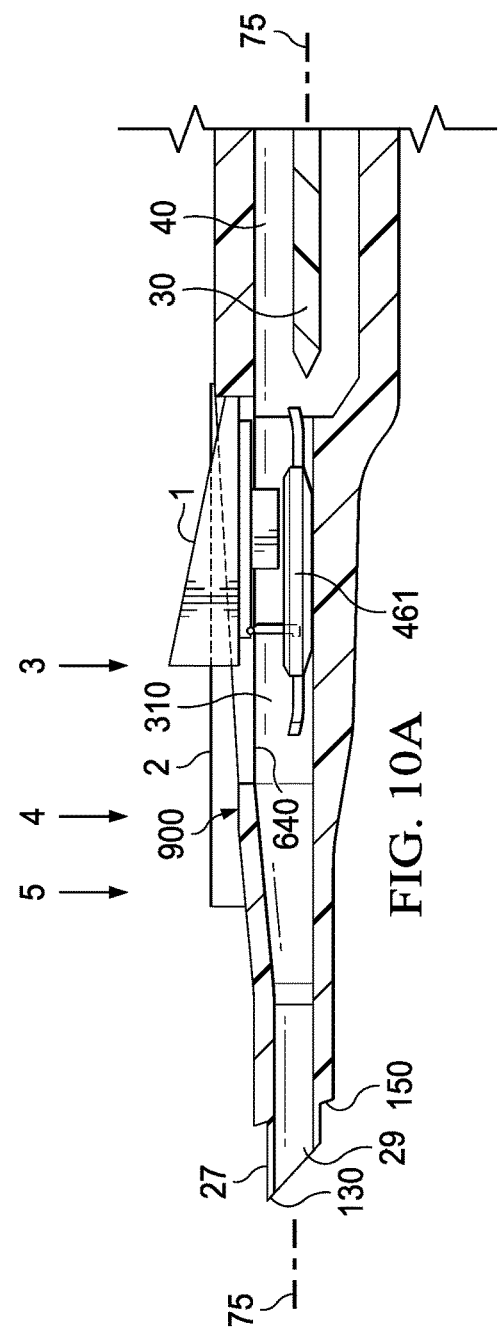
FIG. 10A is a cross-sectional view of an IOL injector having an example compression IOL device with an IOL base.

The IOL compression device is configured such that, in response to an axial movement of the button 1 toward the distal end 902 of the housing 900, the IOL base towing post 7 is adapted to axially pull the IOL base 461 toward the distal end 902 of the housing 900. In response to contacting an interior surface 640 of the tapered IOL compression channel 310, the IOL base 461 is adapted to adopt a compressed configuration. For example, FIG. 8, FIG. 10A, FIG. 10B, and FIG. 10E show the IOL base 461 within the IOL compression device disposed within an IOL injector, prior to the IOL base towing post 7 pulling the IOL base 461 through the tapered IOL compression channel 310. FIG. 10C, FIG. 10D, and FIG. 10F show the IOL base 461 within the IOL compression device disposed within an IOL injector, as the IOL base towing post 7 pulls the IOL base 461 through the tapered IOL compression channel 310. As shown for example in FIG. 10I, the tapered IOL compression channel 310 may have a cross section such as an elliptical cross section 120a. A size of the cross section of the tapered IOL compression channel 310 may vary along its axial length. For example, in some instances, a width W1, a height H1, or both, of the tapered IOL compression channel 310 may change along the axial length of the tapered delivery channel 310. The variation in size of the tapered IOL compression channel 310 may contribute to the compression of the IOL base 461 as the IOL base 461 is advanced therealong through the tapered IOL compression channel 310.

Figure 10B:
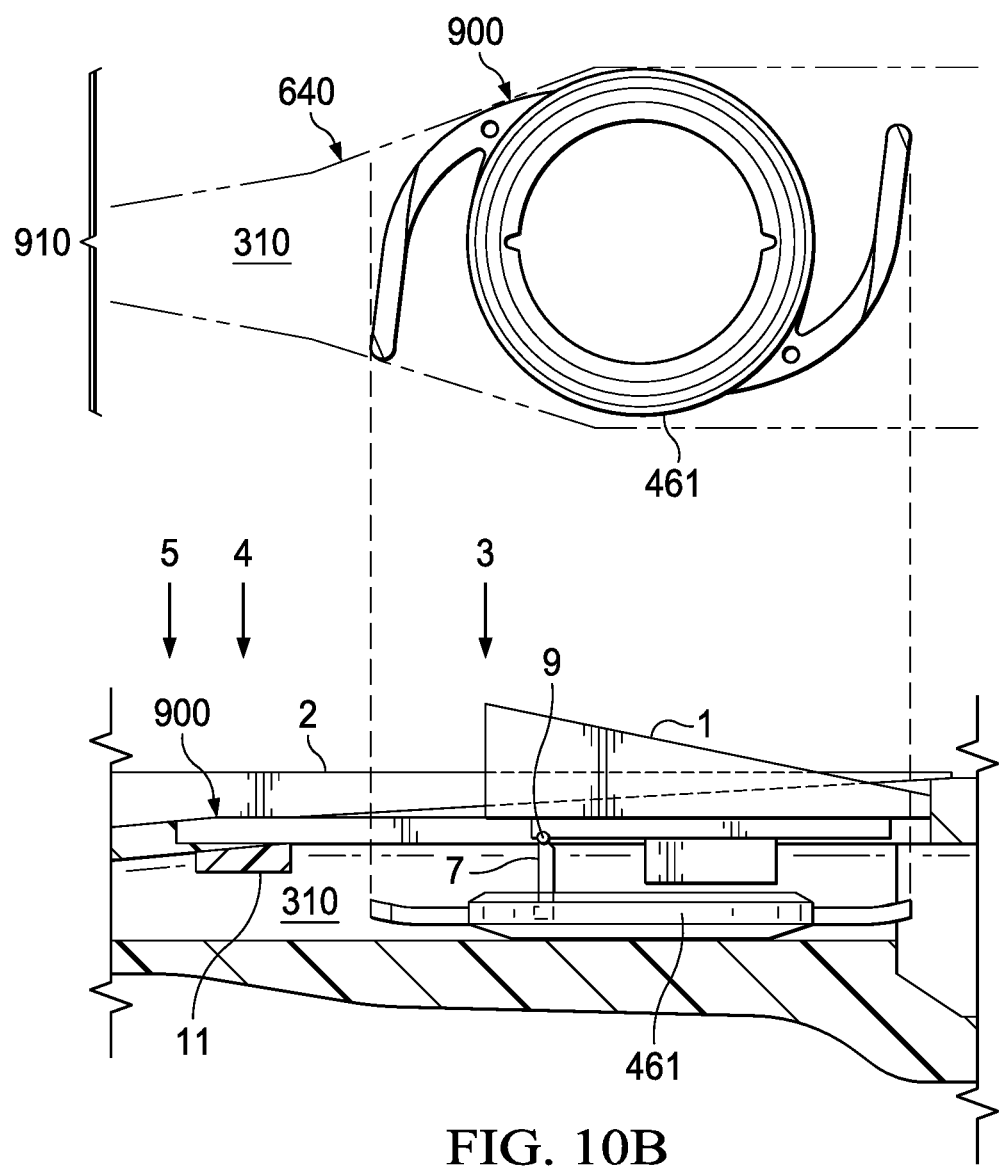
FIG. 10B is a cross-sectional view of an IOL injector having another example IOL compression device with an IOL base.
Figure 10C:
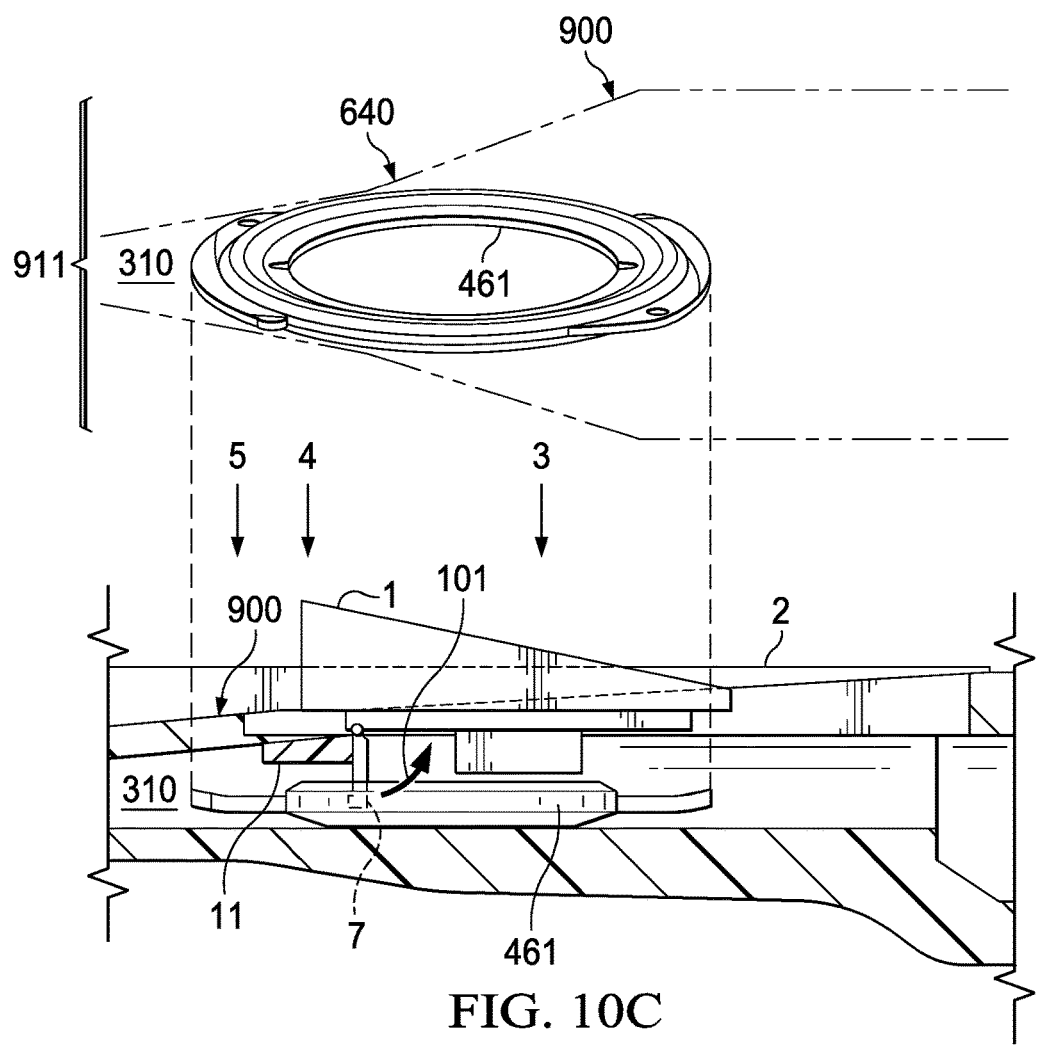
FIG. 10C is another cross-sectional view of an IOL injector having the example IOL compression device of FIG. 10B.
Figure 10D:
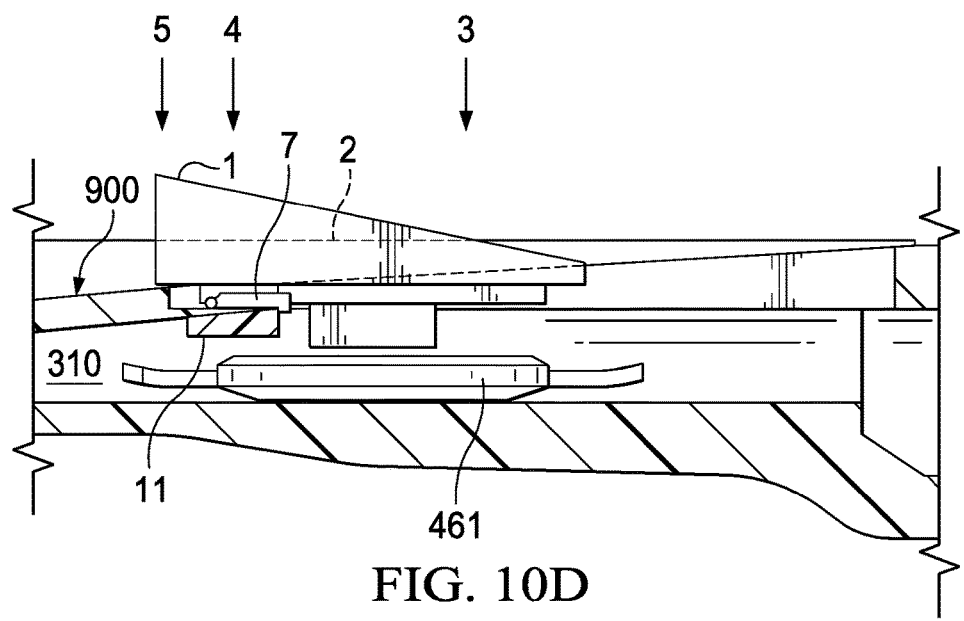
FIG. 10D is another cross-sectional view of an IOL injector having the example IOL compression device of FIG. 10B.

For example, FIG. 10B shows a top down view 910 of an IOL base 461 within the IOL compression device disposed within an IOL injector, prior to the IOL base towing post 7 pulling the IOL base 461 through the tapered IOL compression channel 310. A side view of the same IOL base 461 within the IOL compression device disposed within an IOL injector, prior to the IOL base towing post 7 pulling the IOL base 461 through the tapered IOL compression channel 310, is shown below the top-down view 910.

For example, FIG. 10C shows a top down view 911 of the IOL base 461 within the IOL compression device disposed within an IOL injector, as the IOL base towing post 7 pulls the IOL base 461 through the tapered IOL compression channel 310. A side view of the same IOL base 461 within the IOL compression device disposed within an IOL injector, as the IOL base towing post 7 pulls the IOL base 461 through the tapered IOL compression channel 310 is shown below the top-down view 911.

In some implementations, for example when the IOL compression device is disposed within the nozzle 25 of an IOL injector, the IOL compression device may be configured such that the IOL base 461 is in the IOL storage location 80 when the button 1 is at the proximal position 3, and the IOL base 461 is in the dwell location 809 when the button 1 is at the first distal position 4. For example, FIG. 10A shows in schematic form example locations within the IOL injector 10 of the proximal position 3, the first distal position 4, and a second distal position 5, as further described below.

In some implementations, after the IOL base 461 has adopted a compressed conformation within the IOL compression channel 310, the IOL compression device described herein may be configured to have a collapsible, bendable, foldable or hinged towing post 7, or otherwise be configured such that the towing post 7 is adapted to exit the IOL compression channel 310. For example, when the IOL compression device is disposed within an IOL injector, the IOL compression device may be adapted such that the plunger 30 may axially move through the IOL compression channel 310; accordingly, the towing post 7 may be adapted to exit the IOL compression channel thereby allowing a clear path for the plunger 30 to axially advance the IOL base 461 through the delivery passage, and be delivered to an eye of a patient through the opening 29 of the nozzle 25.

Figure 9:
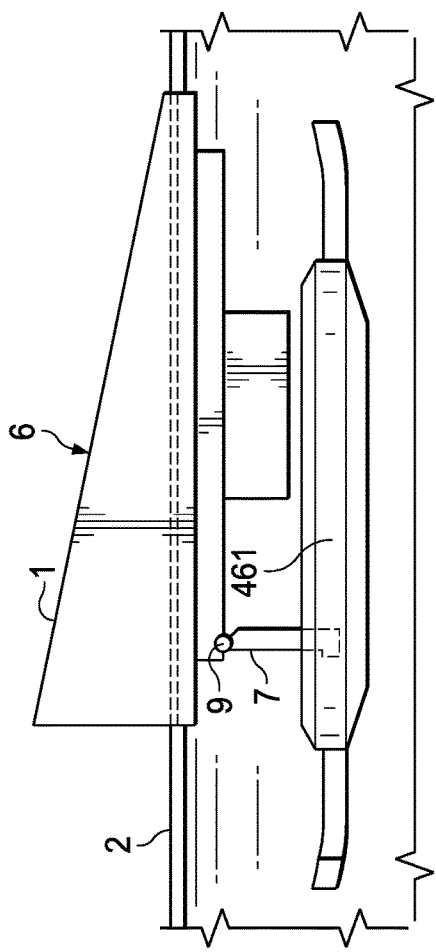
FIG. 9 is a view of an example slidable button of an example IOL compression device with an IOL base.

Accordingly, in some implementations, for example as shown in FIG. 9, FIG. 10A, and FIG. 10B, the IOL towing post 7 may have a hinge 9 configured to allow the towing post 7 to fold, and thereby move out of the IOL compression channel 310 after the IOL base 461 has adopted a compressed conformation within the IOL compression channel 310. In some implementations, the IOL compression channel 310 may include a hard stop 11 contactable by the IOL base towing post 7, such as when the button 1 is in the first distal position 4. FIG. 10B-FIG. 10D shows an example hard stop within the IOL compression channel 310. Accordingly, in some implementations, the track 2 may further include a second distal position 5 distal to the first distal position 4, such that, in response to further axial movement of the slidable button 1 to the second distal position 5, the IOL base towing post 7 is adapted to fold, such as at the hinge 9, for example as shown by arrow 101 in FIG. 10C, causing the IOL base towing post 7 to exit the IOL compression channel 310, for example as shown in FIG. 10D, after the IOL base 461 has adopted the compressed configuration as shown in FIG. 10C. For example, when the IOL compression device is disposed within the nozzle 25 of an IOL injector 10, the plunger 30 may then be advanced axially such that the plunger tip 220 contacts the compressed IOL base 461 and advances the compressed IOL base 461 axially through the opening 29 at the distal end 60 of the nozzle 25.

Figure 10E:
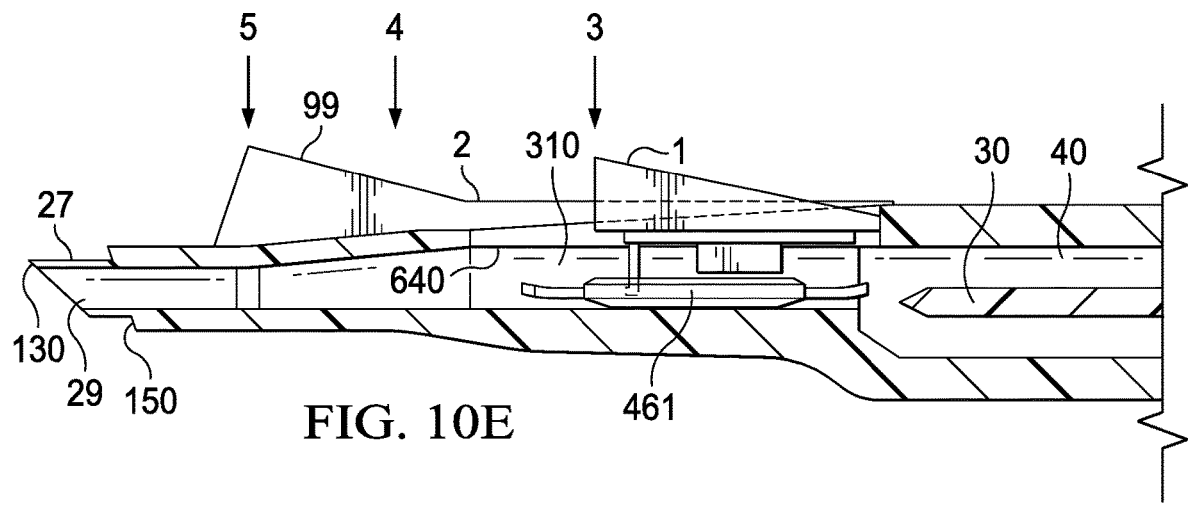
FIG. 10E is a cross-sectional view of an IOL injector having another example IOL compression device with an IOL base.
Figure 10F:
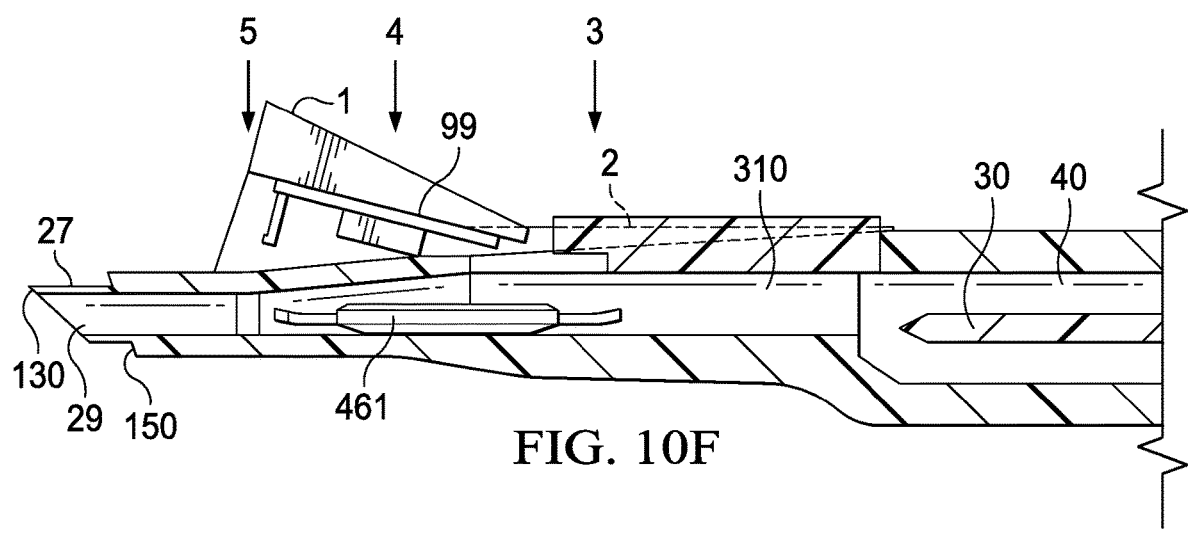
FIG. 10F is another cross-sectional view of an IOL injector having the example IOL compression device of FIG. 10E.

In some implementations, for example as shown in FIG. 10E-FIG. 10F, a portion of the track 2, such as between the first distal position 4 and the second distal position 5 may include a ramp 99 having a slope that inclines away from the IOL compression channel 310. In such implementations, the towing post 7 may not include a hinge 9 to fold the towing post 7 out of the IOL compression channel 310, but rather, in response to an axial movement of the slidable button 1 along the ramp 99, for example to the second distal position 5, the IOL base towing post 7 may exit the IOL compression channel 310 after the IOL base 461 adopts the compressed configuration for example as shown in FIG. 10C. FIG. 10E-FIG. 10F illustrate an example operation of an IOL compression device of the present disclosure having a ramp 99 configured such that the IOL towing post 7 is adapted to move out of the IOL compression channel 310. For example, when the IOL compression device is disposed within the nozzle 25 of an IOL injector 10, the plunger 30 may then be advanced axially such that the plunger tip 220 contacts the compressed IOL base 461 and advances the compressed IOL base 461 axially through the opening 29 at the distal end 60 of the nozzle 25.

Figure 10G:
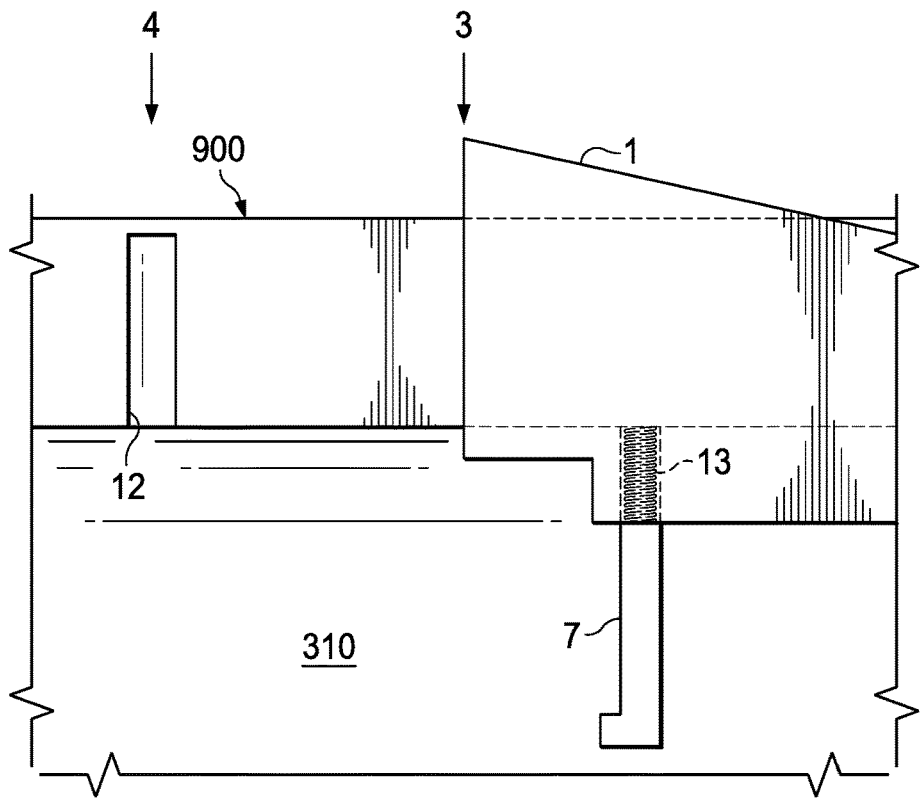
FIG. 10G is a cross-sectional view of another example IOL compression device.
Figure 10H:
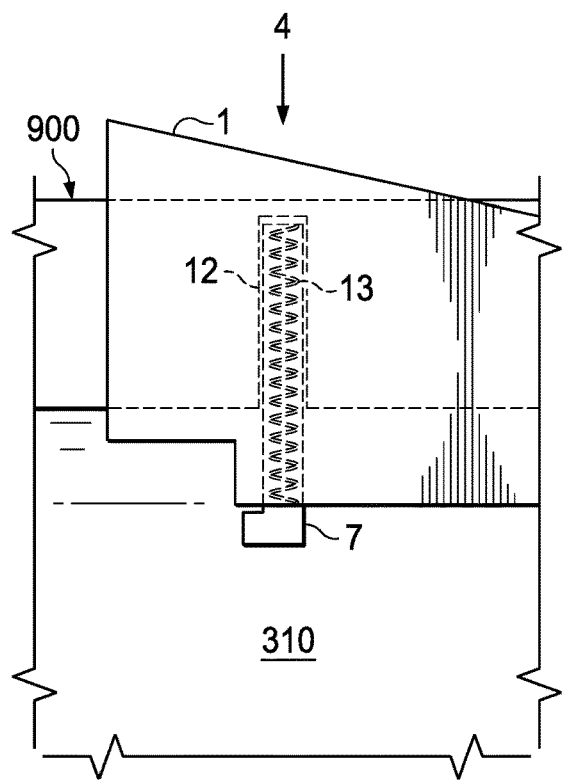
FIG. 10H is another cross-sectional view of the example IOL compression device of FIG. 10G.
Figure 10I:
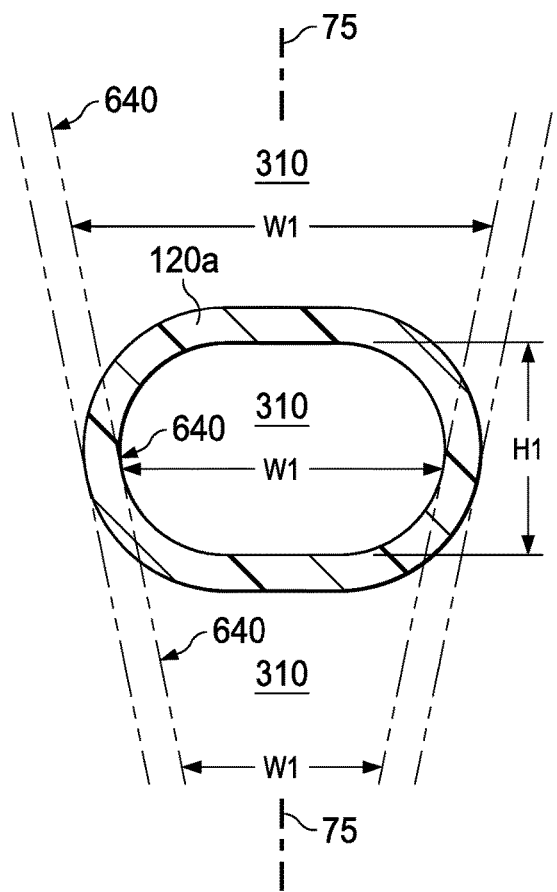
FIG. 10I is a schematic of a portion of an example tapered IOL compression channel.

In other implementations, the IOL compression device may include a spring mechanism configured to move the towing post 7 out of the IOL compression channel 310 after the IOL base 461 has adopted a compressed configuration. For example, FIG. 10G-FIG. 10H show in schematic form an example IOL compression device, in which the IOL compression device includes a recess 12 sized to receive the IOL base towing post 7. For example, the recess 12 may be located at the first distal position 4. The button 1 may further include a spring 13 adapted to move the IOL towing post 7 into the recess 12. The spring 13 may have a first end coupled to the button 1 and a second end coupled to the IOL towing post 7, such that in response to an axial movement of the slidable button 1 to the first distal position 4, the IOL towing post 7 is movable, such as transversely movable, into the recess 12 in response to movement of the spring 13 and thereby exits the IOL compression channel 310 after the IOL base 461 adopts a compressed configuration. For example, the spring 13 in FIG. 10G-FIG. 10H is a compression spring that is compressed and has stored elastic energy in FIG. 10G. In response to an axial movement of the slidable button 1 to the first distal position 4, the IOL towing post 7 is transversely movable into the recess 12 in response to release of the stored elastic energy of the spring 13, such as elongation of the compression spring as shown in FIG. 10H, and thereby exits the IOL compression channel 310 after the IOL base 461 adopts a compressed configuration. For example, when the IOL compression device is disposed within the nozzle 25 of an IOL injector 10, the plunger 30 may then be advanced axially such that the plunger tip 220 contacts the compressed IOL base 461 and advances the compressed IOL base 461 axially through the opening 29 at the distal end 60 of the nozzle 25.

In some implementations, as shown in FIG. 3B, the inner edge 8 of the IOL base 461 may include a groove 14 disposed within the circumference of the inner edge 8. Accordingly, the second end of the IOL base towing post 7 may have a size and shape adapted to insert into the groove 14 in the distal inner edge 8 of the IOL base 461, thereby providing a more stable contact or coupling between the second end of the towing post 7 and the IOL base 461. The groove 14 therefore has utility for the assembly of the optic 460 onto the base 461, as described above, and also synergistic and/or unexpected function allowing the contact or coupling of the towing post 7 to the IOL base 461 in accordance with the use of the IOL compression device of the present disclosure. Furthermore, in some implementations, the distal inner edge 8 of the IOL base 461 may include a notch 15 and the second end of the IOL base towing post 7 has a size and shape adapted to insert into the notch 15, also providing a more stable contact or coupling between the second end of the towing post 7 and the IOL base 461. Similarly, the notch 15 therefore also has utility for the assembly of the optic 460 onto the base 461, as described above, and also synergistic and/or unexpected function allowing the contact or coupling of the towing post 7 to the IOL base 461 in accordance with the use of the IOL compression device of the present disclosure. The notch 15 may provide control for compression of the base 461, keeping the base 461 in an axial configuration as it becomes compressed and moves axially within the bore 40, and maintaining the haptics 450 in a consistent position.

In some implementations, the slidable button 1 may further include a second post 18a having a first end coupled to a proximal portion of the slidable button 1. The second post 18a is coupled to the slidable button 1 at a first distance from the IOL base towing post 7 such that when the IOL base towing post 7 contacts the distal inner edge 8 of the IOL base 461, the second post 18a is proximally adjacent to a trailing haptic 450 of the IOL base 461.

In some implementations, the second post 18a is adapted to guide the trailing haptic 450, preventing the trailing haptic 450 from extending proximally away from the IOL base 461 and dragging behind the IOL base 461, thereby maintain the trailing haptic 450 in contact with the IOL base 450 to adopt an optimal compressed configuration.

Figure 12:
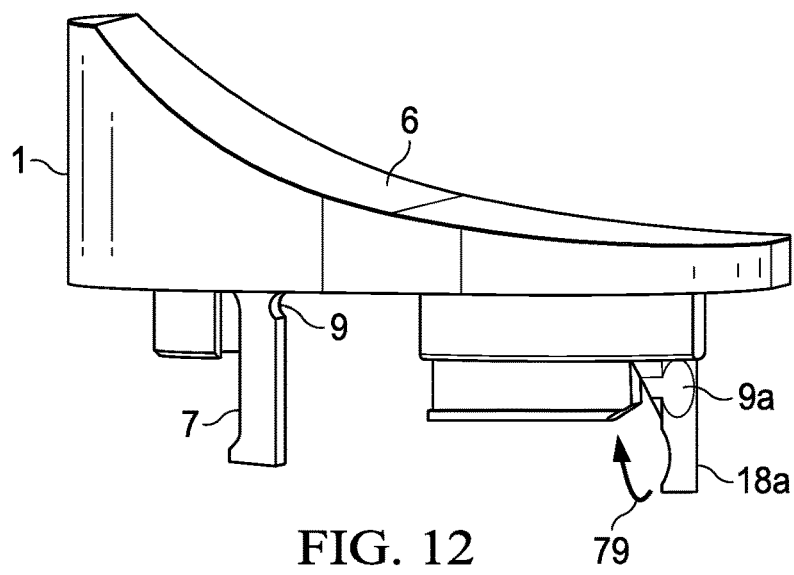
FIG. 12 is a schematic of an example slidable button having an IOL base towing post and a second post.

FIG. 12 is a schematic of an example slidable button 1 having a second post 18a. In some implementations, such as shown in FIG. 12, the second post 18a may include a hinge 9a configured to allow the second post 18a to fold laterally, such as in the direction of arrow 79 in FIG. 12, such that the second post 18a exits the path of the plunger rod 210 through the compression channel 310, and thereby does not block axial movement of the plunger rod 210 through the compression channel 310. For example, in some implementations, the hinge 9a is configured to allow the second post 18a to fold laterally, in response to being contacted by the plunger tip 220 upon axial plunger 30 advancement, as the plunger 30 moves axially through the compression channel 310, after the IOL base 461 has adopted the compressed conformation. Accordingly, following the exit of the second post 18a from the path of the plunger rod 210 within the compression channel 310, the plunger 30 may further axially advance the IOL base 461 through the nozzle 25 to implant in an eye of a patient.

Figure 13:
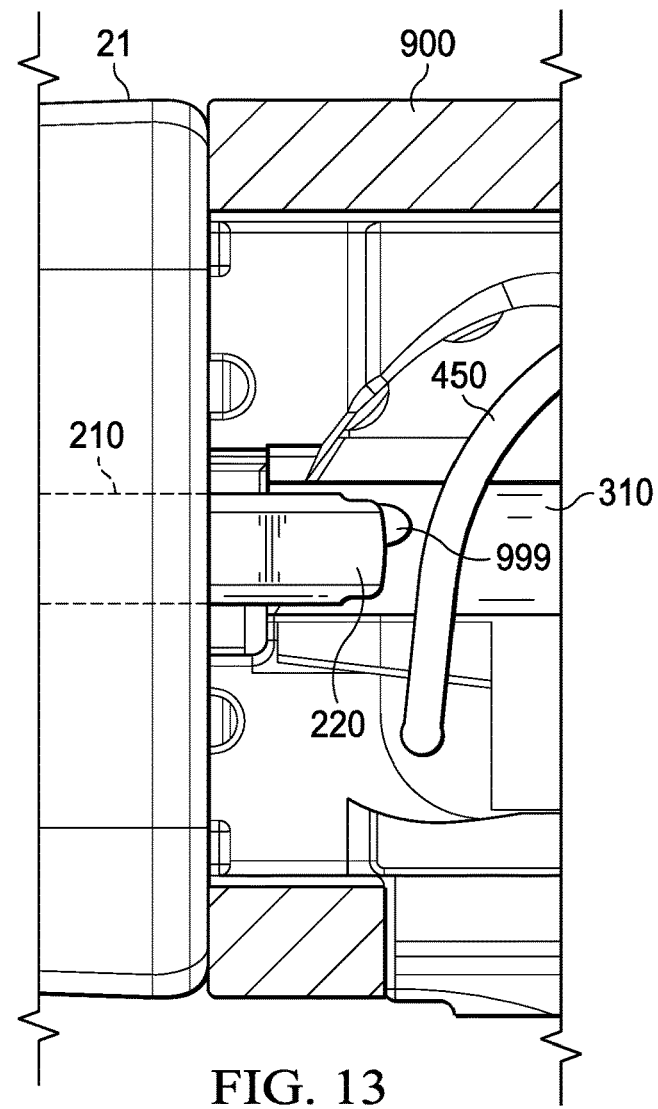
FIG. 13 is a schematic of an example plunger 30 disposed within an IOL injector.

In some implementations, such as shown in FIG. 13, the plunger tip 220 may be adapted such that it has a second post contact knob 999 adapted to contact the second post 18a during axial advancement of the plunger 30 as the plunger tip 220 moves axially through the compression channel, and upon contact causes the second post 18 to fold laterally out of the path of the plunger 30 within the compression channel 310. The second post contact knob 999 may be a distally extending structure shaped, such as curved or tapered, and of a size such that during advancement of the plunger 30, the knob 999 smoothly pushes the second post 18a causing the second post 18a to fold about the hinge 9a thereby causing the second post 18a to fold out of the path of the plunger 30 axial advancement within the compression channel 310.

Figure 11A:
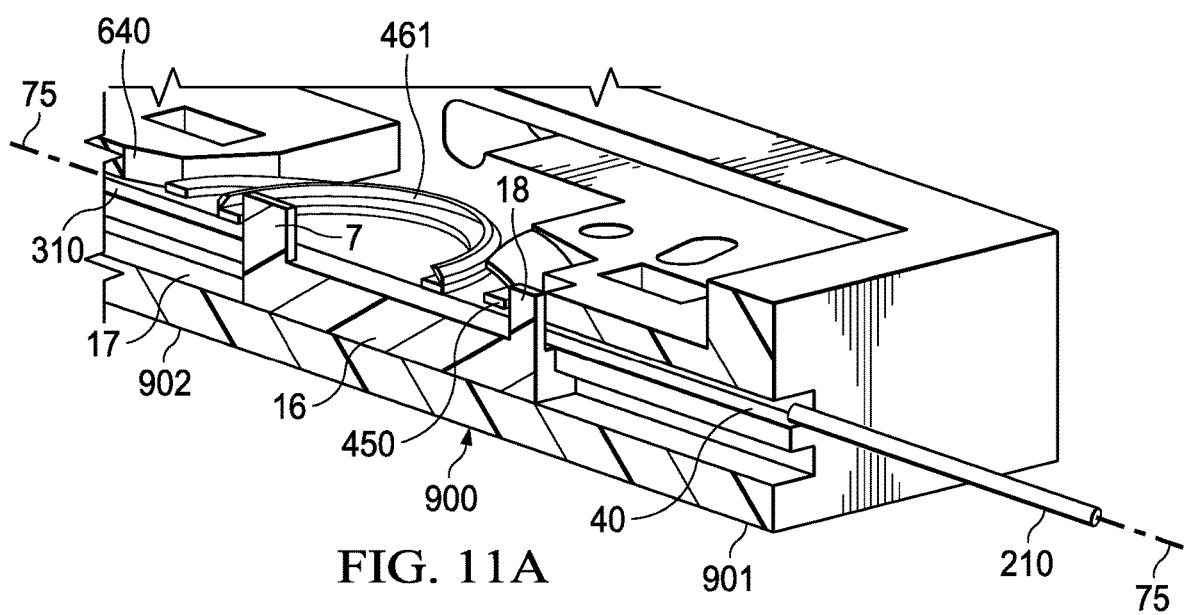
FIG. 11A is a view of another example embodiment of an IOL compression device with an IOL base.

Turning now to FIG. 11A-FIG. 11E, in some implementations, the IOL compression device may be configured such that, when disposed within an IOL injector, the IOL compression device has an IOL towing post movable in response to an axial force applied to the plunger 30, rather than in response to a slidable button 7. Accordingly, for example as shown in FIG. 11A, in some implementations, the IOL compression device may have a slidable beam 16 movably coupled within a beam track 17 disposed within the housing 900. The slidable beam 16 is axially slidable within the beam track 17, such as between a proximal position 3 and a first distal position 4, and further slidable axially to a second proximal position 5, for example as shown in FIG. 11B-FIG. 11E. The beam track 17 has a longitudinal axis substantially aligned with and adjacent to the longitudinal axis 75 of the IOL compression channel 310. For example, as shown in FIG. 11A, the beam track 17 may be disposed within the housing 900 below the IOL compression channel 310, such that the slidable beam 16 may slide axially below the IOL compression channel 310. Other configurations are possible, such as having the beam track 17 disposed within the housing 900 of the IOL compression device above the IOL compression channel 310 or disposed laterally to the IOL compression channel 310 within the housing 900 of the IOL compression device.

In some implementations, the slidable beam 16 has an IOL base towing post 7 having a first end coupled to a distal portion of the slidable beam 16 and a second end adapted to contact or couple to a distal inner edge 8 of an IOL base 461. The slidable beam 16 also has a second post 18 having a first end coupled to a proximal portion of the slidable beam 16. The second post 18 is coupled to the slidable beam 16 at a first distance from the IOL base towing post 7 such that when the IOL base towing post 7 contacts the distal inner edge 8 of the IOL base 461, the second post 18 is proximally adjacent to a trailing haptic 450 of the IOL base 461.

Accordingly, in some implementations, in response to an axial force applied to the second post 18 toward the distal end 902 of the housing 900, the slidable beam 16 is adapted to slide axially within the beam track 17 toward the distal end 902 of the housing 900, the IOL towing post 7 is adapted to pull the IOL base 70 toward the distal end 902 of the housing 900, and in response to contacting the interior surface 640 of the IOL compression channel 310, the IOL base 461 is adapted to adopt a compressed configuration.

In some implementations, when the IOL compression device is disposed within an IOL injector, the IOL compression device is configured such that, in response to an axial force applied to the plunger, such as applied to the flanges 240, upon an axial movement of the plunger 30 toward the distal end 60 of the IOL injector body 20, the plunger tip 220 is adapted to contact the second post 18, thereby pushing the slidable beam 16 axially along the beam track 17. As the slidable beam 16 slides axially within the beam track 17 toward the distal end 60 of the IOL injector 10, the IOL towing post 7 is adapted to contact or couple to the distal inner edge 8 of the IOL base 461, and thereby tow the IOL base 70 toward the distal end 60 of the nozzle 25. As the IOL base 461 moves axially within the tapered IOL compression channel 310, in response to contacting an interior surface 640 of the IOL compression channel 310, the IOL base 461 is adapted to adopt a compressed configuration.

Figure 11B:
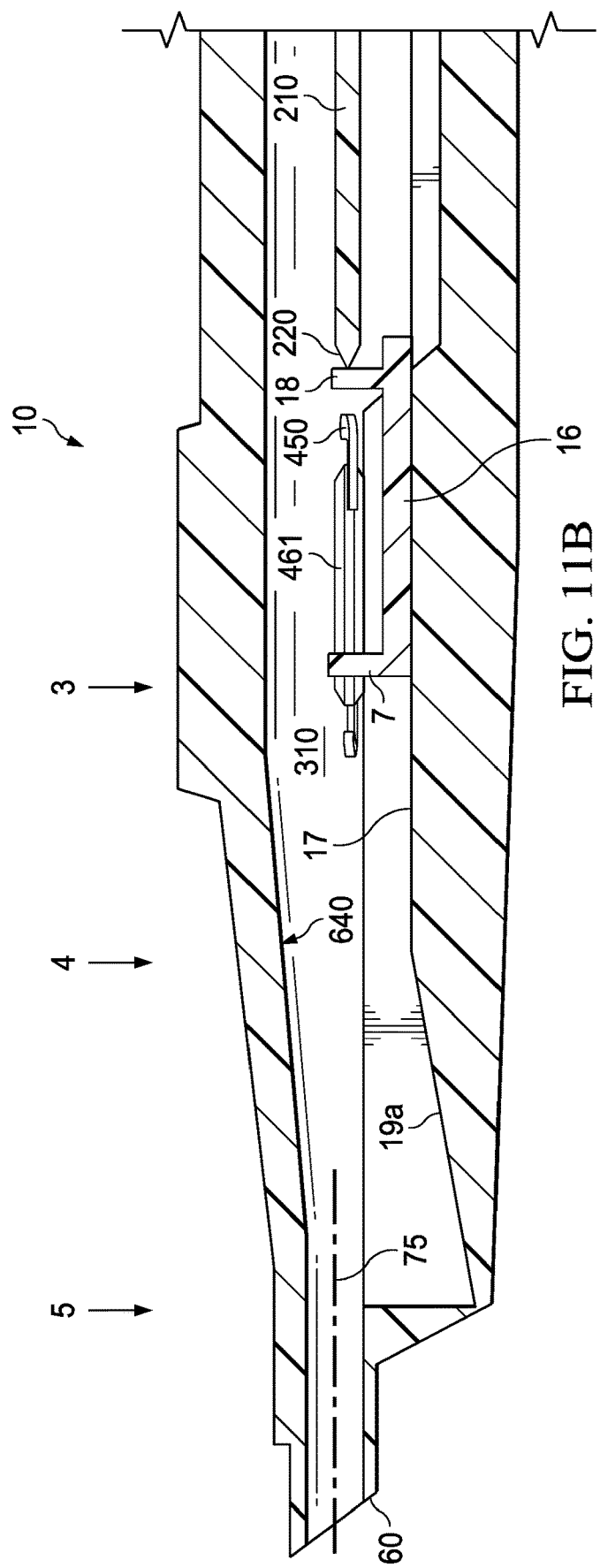
FIG. 11B is a cross-sectional view of an example embodiment of the IOL compression device of FIG. 11A disposed within an IOL injector with an IOL base.
Figure 11C:
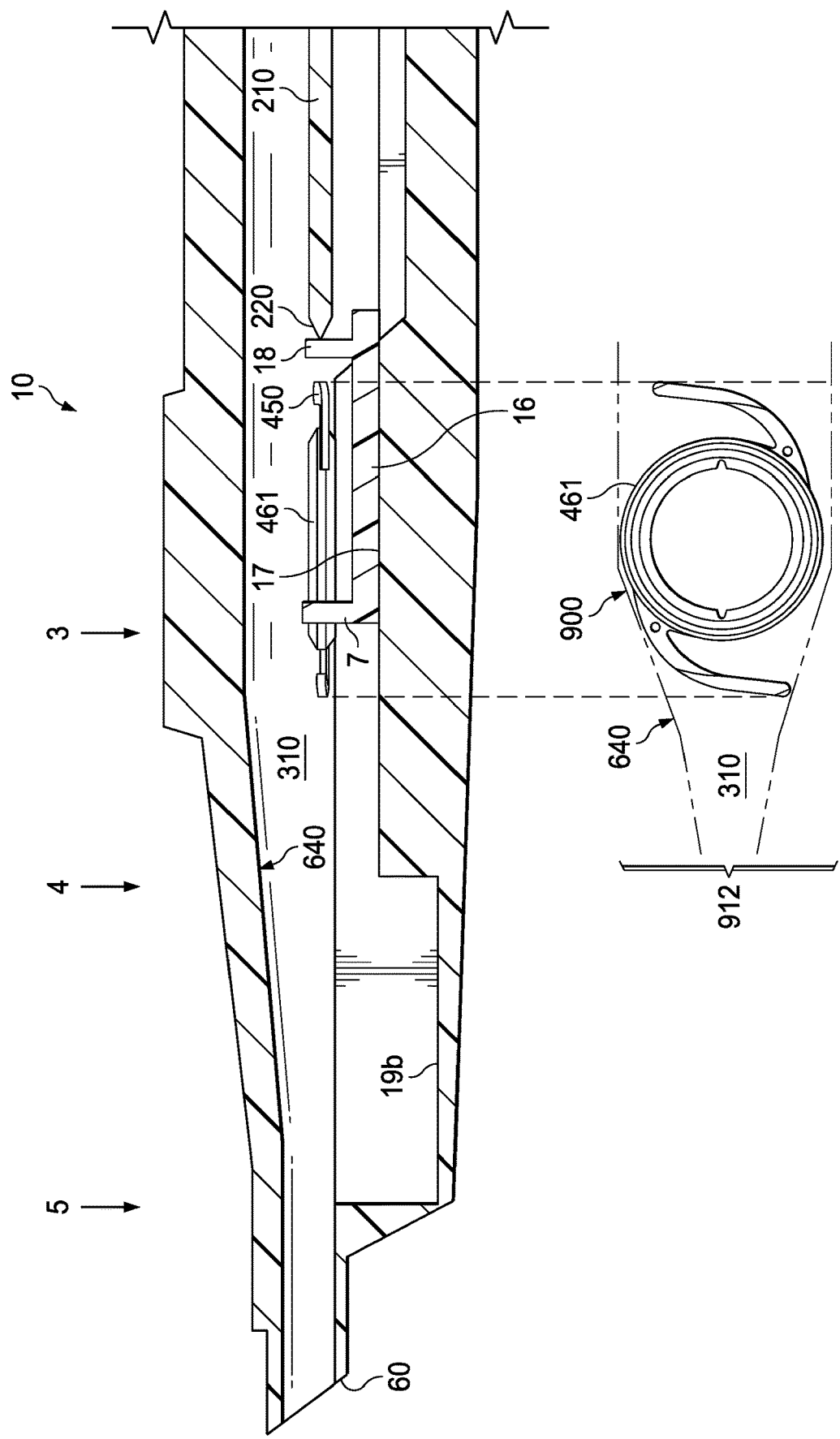
FIG. 11C is a cross-sectional view of another example embodiment of the IOL compression device of FIG. 11A disposed within an IOL injector with an IOL base.

For example, FIG. 11C shows a top down view 912 of an IOL base 461 within the IOL compression device disposed within an IOL injector, prior to the IOL base towing post 7 pulling the IOL base 461 through the tapered IOL compression channel 310. A side view of the same IOL base 461 within the IOL compression device disposed within an IOL injector, prior to the IOL base towing post 7 pulling the IOL base 461 through the tapered IOL compression channel 310, is shown above the top-down view 912.

Figure 11D:
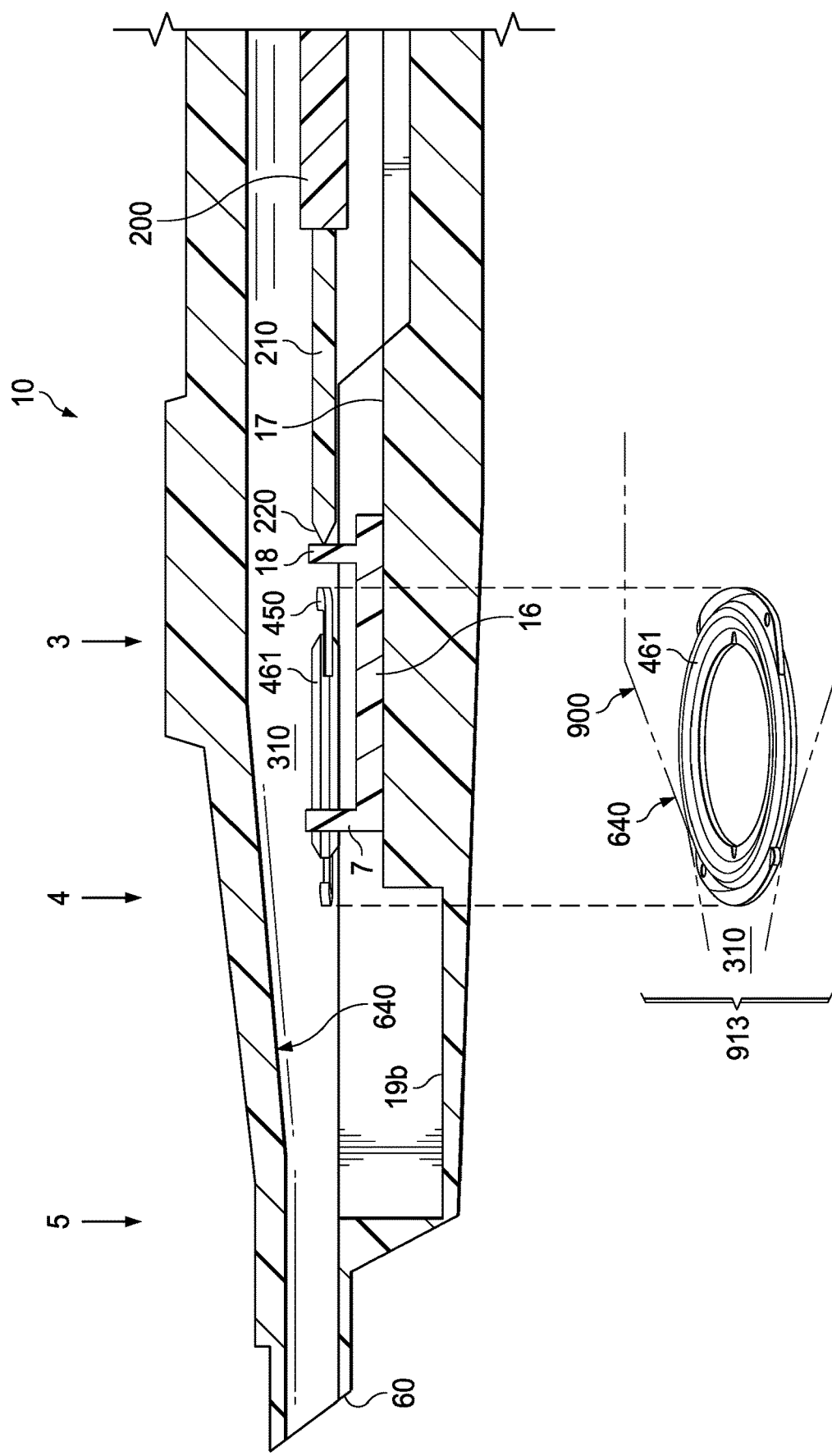
FIG. 11D is another view of the IOL compression device of FIG. 11C disposed within an IOL injector with an IOL base.

For example, FIG. 11D shows a top down view 913 of the IOL base 461 within the IOL compression device disposed within an IOL injector, as the IOL base towing post 7 pulls the IOL base 461 through the tapered IOL compression channel 310. A side view of the same IOL base 461 within the IOL compression device disposed within an IOL injector, as the IOL base towing post 7 pulls the IOL base 461 through the tapered IOL compression channel 310, is shown above the top-down view 913.

In some implementations, when the IOL compression device is disposed within an IOL injector, the IOL compression device having the slidable beam 16 may be configured such that the IOL base 461 is in the IOL storage location 80 when the slidable beam 16 is at the proximal position 3 and the IOL base 461 is in the dwell location 809 when the slidable beam 16 is at the first distal position 4.

FIG. 11B-FIG. 11E are schematics of an example IOL compression device of the present disclosure disposed within an IOL injector and having a well 19a or 19b configured such that the IOL towing post 7 coupled to the slidable beam 16 is adapted to move out of the IOL compression channel 310 after the IOL base 461 adopts the compressed configuration, for example as shown in FIG. 11D, thereby allowing the plunger tip 220 to contact the IOL base 461 and move the IOL base 461 axially through the delivery passage. In some implementations, for example as shown in FIG. 11B, a portion of the beam track 17 further includes a second distal position 5 distal to the first distal position 4 and the slidable beam 16 is further axially slidable to the second distal position 5. In some implementations, such as shown in FIG. 11B, a portion of the beam track 17 between the first distal position 4 and the second distal position 5 may have a well 19a having a slope that inclines away from the tapered IOL compression channel 310. Accordingly, in response to a further axial movement of the slidable beam 16, such as in response to further axial movement of the plunger 30, the slidable beam 16 is adapted to slide to the second distal position 5 along the well 19a. The IOL base towing post 7 and the second post 18 accordingly are adapted to exit the IOL compression channel 310 after the IOL base 461 adopts the compressed configuration. After the second towing post 18 exits the deliver channel, the plunger tip 220 is adapted to contact the IOL base 461. The plunger 30 may then be further advanced axially to deliver the IOL base 461 through the opening 29 at the distal end 60 of the nozzle 25.

Figure 11E:
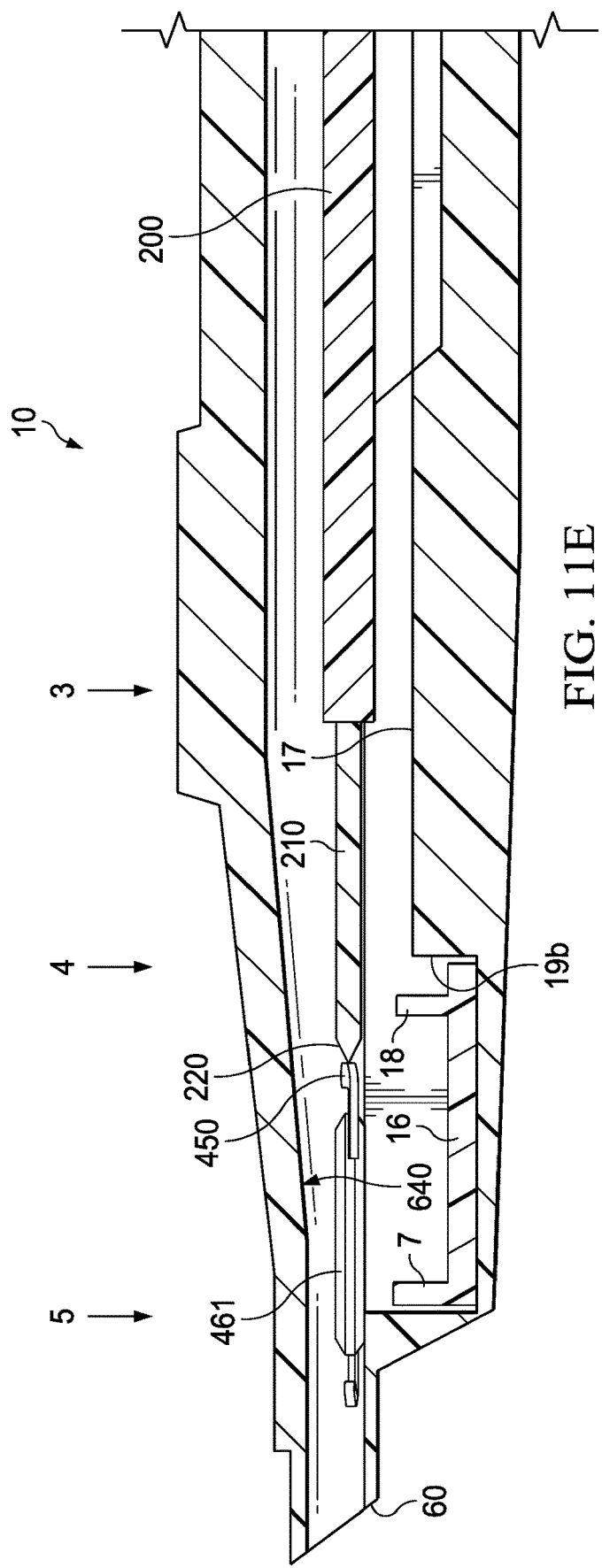
FIG. 11E is another view of the IOL compression device of FIG. 11C disposed within an IOL injector with an IOL base.

In some implementations, for example as shown in FIG. 11C-FIG. 11E, a portion of the beam track 17, such as between the first distal position 4 and the second distal position 5 may include a well 19b sized to receive the slidable beam 16. Accordingly, in response to further axial movement of the plunger 30, the slidable beam 16 is adapted to slide to the second distal position 5 and enter the well 19b. The IOL base towing post 7 and the second post 18 are thereby configured to exit the IOL compression channel 310 after the IOL base 461 adopts the compressed configuration. After the second towing post 18 exits the IOL compression channel 310, the plunger tip 220 is adapted to contact the IOL base 461 and/or the trailing haptic 450. The plunger 30 may then be further advanced axially to deliver the IOL base 461 through the opening 29 at the distal end 60 of the nozzle 25.

In some implementations, the inner edge 8 of the IOL base 461 may include a groove 14 disposed within the circumference of the inner edge 8 and the second end of the IOL base towing post 7 of the slidable beam 16 may have a size and shape adapted to insert into the groove 14 in the distal inner edge 8 of the IOL base 461. In some implementations, the distal inner edge 8 of the IOL base 461 further includes a notch 15 and the second end of the IOL base towing post 7 has a size and shape adapted to insert into the notch 15.

In some implementations, the second post 18 of the slidable beam 16 is adapted to guide the trailing haptic 450, preventing the trailing haptic 450 from extending proximally away from the IOL base 461 and dragging behind the IOL base 461, thereby maintain the trailing haptic 450 in contact with the IOL base 450 to adopt an optimal compressed configuration.

Non-limiting examples of IOL injectors that may be adapted according to the present disclosure include those described in U.S. Pat. No. 7,156,854 and U.S. Patent Application Publication No. 2016/0256316, the disclosures of each being incorporated herein by reference in their entireties.

The above disclosed subject matter is to be considered illustrative, and not restrictive, and the appended claims are intended to cover all such modifications, enhancements, and other implementations which fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An IOL compression device, comprising:
   a housing having a proximal end and a distal end, and a track disposed on a first side of the housing;
   a tapered IOL compression channel disposed within the housing and having a longitudinal axis extending from the proximal end to the distal end;
   a slidable button movably coupled within the track, the slidable button axially slidable between a proximal position and a first distal position, the track having a longitudinal axis substantially aligned with and adjacent to the tapered IOL compression channel, the slidable button having:
   a pad accessible to a user and adapted to receive an axial force; and
   an IOL base towing post adapted to extend substantially perpendicular to the tapered IOL compression channel, the IOL base towing post having a first end coupled to the slidable button and a second end adapted to contact a distal inner edge of an IOL base when the IOL base is in the tapered IOL compression channel;

wherein in response to an axial movement of the slidable button toward the distal end of the housing:
the IOL base towing post is adapted to axially pull the IOL base through the tapered IOL compression channel toward the distal end of the housing; and
in response to contacting an interior surface of the tapered IOL compression channel, the IOL base is adapted to adopt a compressed configuration.

2. The IOL compression device of claim 1, wherein: the IOL base towing post further comprises a hinge;
the tapered IOL compression channel further comprises a hard stop disposed within the tapered IOL compression channel at the distal end of the housing and contactable by the IOL base towing post when the slidable button is in the first distal position;
the track further comprises a second distal position distal to the first distal position; and
the slidable button is further axially slidable to the second distal position;
wherein in response to an axial movement of the slidable button to the second distal position, the IOL base towing post is adapted to fold at the hinge in response to contacting the hard stop and the IOL base towing post is thereby configured to exit the tapered IOL compression channel after the IOL base adopts the compressed configuration.

3. The IOL compression device of claim 1, wherein:
the track further comprises a second distal position distal to the first distal position; the slidable button is further axially slidable to the second distal position; and
a portion of the track between the first distal position and the second distal position comprises a ramp having a slope that inclines away from the tapered IOL compression channel;
wherein in response to an axial movement of the slidable button along the ramp to the second distal position, the IOL base towing post is adapted to exit the tapered IOL compression channel after the IOL base adopts the compressed configuration.

4. The IOL compression device of claim 1, wherein:
the housing further comprises a recess sized to receive the IOL base towing post, the recess located at the first distal position;
the slidable button further comprises a spring adapted to move the IOL towing post into the recess, the spring having a first end coupled to the slidable button and a second end coupled to the IOL base towing post;
wherein in response to an axial movement of the slidable button to the first distal position, the IOL base towing post is transversely movable into the recess in response to movement of the spring and thereby exits the tapered IOL compression channel after the IOL base adopts a compressed configuration.

5. The IOL compression device of claim 1, wherein:
the distal inner edge of the IOL base further comprises a groove disposed within a circumference of the distal inner edge and the second end of the IOL base towing post has a size and shape adapted to insert into the groove in the distal inner edge of the IOL base.

6. The IOL compression device of claim 1, wherein:
the distal inner edge of the IOL base further comprises a notch and the second end of the IOL base towing post has a size and shape adapted to insert into the notch.

7. The IOL compression device of claim 1, wherein:
the slidable button further comprises a second towing post having a first end coupled to a proximal portion of the slidable button, wherein the second towing post is coupled to the slidable button at a first distance from the IOL base towing post such that when the IOL base towing post contacts the distal inner edge of the IOL base, the second towing post is proximally adjacent to a trailing haptic of the of the IOL base.

8. The IOL compression device of claim 7, wherein:
the second towing post further comprises a hinge adapted to fold laterally in response to contacting a plunger tip moving axially through tapered IOL the compression channel, the second towing post thereby configured to exit the tapered IOL compression channel.

9. The IOL compression device of claim 1, wherein the IOL compression device is adapted to be fixedly disposed within or removably disposed within an IOL injector.

10. The IOL compression device of claim 9, wherein the IOL injector comprises: an injector body having:
a main body having a proximal end and a distal end;
a nozzle having a proximal end and a distal end, the proximal end of the nozzle coupled to the distal end of the main body; the nozzle having an IOL storage location configured to house an uncompressed IOL, and an IOL dwell location distal to the IOL storage location;
a bore having a longitudinal axis extending from the proximal end of the main body to the distal end of the nozzle; and
a plunger movably coupled within the injector body and aligned within the bore, the plunger having a plunger tip adapted to contact an IOL.

11. The IOL compression device of claim 10, wherein the IOL compression device is disposed within the nozzle.

12. The IOL compression device of claim 10, wherein the IOL compression device is configured such that:
the IOL base is in an IOL storage location when the slidable button is at the proximal position; and
the IOL base is in the IOL dwell location when the slidable button is at the first distal position.

13. The IOL compression device of claim 10, wherein:
the tapered IOL compression channel is coupled to and aligned with the bore; and the plunger is axially movable through the tapered IOL compression channel.

14. An IOL compression device, comprising:
a housing having a proximal end and a distal end, and a beam track disposed on a first side of the housing;
a tapered IOL compression channel disposed within the housing and having a longitudinal axis extending from the proximal end to the distal end;
a slidable beam movably coupled within the beam track, the slidable beam axially slidable therein between a proximal position and a first distal position, the beam track having a longitudinal axis substantially aligned with and adjacent to the tapered IOL compression channel, the slidable beam having: an IOL base towing post adapted to extend substantially perpendicular to the tapered IOL compression channel, the IOL base towing post having a first end coupled to a distal portion of the slidable beam and a second end adapted to contact a distal inner edge of an IOL base when the IOL base is in the tapered IOL compression channel; and
a second towing post having a first end coupled to a proximal portion of the slidable beam, wherein the second towing post is coupled to the slidable beam at a first distance from the IOL base towing post such that when the IOL base towing post contacts the distal inner edge of the IOL base, the second towing post is proximally adjacent to a trailing haptic of the IOL base;

wherein in response to an axial force applied to the second towing post toward the distal end of the housing:
the slidable beam is adapted to slide axially within the beam track toward the distal end of the housing;
the IOL base towing post is adapted to pull the IOL base through the tapered IOL compression channel toward the distal end of the housing; and
in response to contacting an interior surface of the tapered IOL compression channel, the IOL base is adapted to adopt a compressed configuration.

15. The IOL compression device of claim 14, wherein:
the beam track further comprises a second distal position distal to the first distal position; the slidable beam is further axially slidable to the second distal position; and
a portion of the beam track between the first distal position and the second distal position comprises a well sized to receive the slidable beam;
wherein in response to a further axial movement of the slidable beam to the second distal position:
the slidable beam is adapted to enter the well; and
the IOL base towing post and the second towing post are configured to exit the tapered IOL compression channel after the IOL base adopts the compressed configuration.

16. The IOL compression device of claim 14, wherein:
the distal inner edge of the IOL base further comprises a groove disposed within a circumference of the distal inner edge and the second end of the IOL base towing post has a size and shape adapted to insert into the groove in the distal inner edge of the IOL base.

17. The IOL compression device of claim 14, wherein:
the distal inner edge of the IOL base further comprises a notch and the second end of the IOL base towing post has a size and shape adapted to insert into the notch.

18. The IOL compression device of claim 14, wherein the IOL compression device is adapted to be fixedly disposed within or removably disposed within an IOL injector.

19. The IOL compression device of claim 18, wherein the IOL injector comprises: an injector body having:
a main body having a proximal end and a distal end;
a nozzle having a proximal end and a distal end, the proximal end of the nozzle coupled to the distal end of the main body; the nozzle having an IOL storage location configured to house an uncompressed IOL, and an IOL dwell location distal to the IOL storage location;
a bore having a longitudinal axis extending from the proximal end of the main body to the distal end of the nozzle; and
a plunger movably coupled within the injector body and aligned within the bore, the plunger having a plunger tip adapted to contact an IOL.

20. The IOL compression device of claim 19, wherein the IOL compression device is disposed within the nozzle.

21. The IOL compression device of claim 19, wherein the IOL compression device is configured such that:
the IOL base is in an IOL storage location when the slidable beam is at the proximal position; and
the IOL base is in a dwell location when the slidable beam is at the first distal position.

22. The IOL compression device of claim 19, wherein:
the tapered IOL compression channel is coupled to and aligned with the bore; and the plunger is axially movable through the tapered IOL compression channel;
wherein in response to an axial movement of the plunger toward the distal end of the nozzle:
the plunger tip is adapted to contact the second towing post;
the slidable beam is adapted to slide axially within the beam track to a first distal position;
the IOL base towing post is adapted to pull the IOL base toward the distal end of the nozzle; and
in response to contacting an interior surface of the tapered IOL compression channel, the IOL base is adapted to adopt a compressed configuration.

23. The IOL compression device of claim 22, wherein:
a portion of the beam track between the first distal position and a second distal position distal to the first distal position comprises a well sized to receive the slidable beam;
wherein in response to a further axial movement of the plunger toward the distal end of the nozzle:
the slidable beam is adapted to enter the well;
the IOL base towing post and the second towing post are adapted to exit the tapered IOL compression channel after the IOL base adopts the compressed configuration; and
the plunger tip is adapted to contact the IOL base, such that the plunger is adapted to axially advance the IOL to exit the distal end of the nozzle.

* * * * *